United States Patent [19]

Fujibayashi et al.

[11] Patent Number: 5,283,124
[45] Date of Patent: Feb. 1, 1994

[54] COATING RESIN COMPOSITION

[75] Inventors: Toshio Fujibayashi; Haruo Nagaoka, both of Hiratsuka, Japan

[73] Assignee: Kansai Paint Co., Ltd., Hyogo, Japan

[21] Appl. No.: 662,571

[22] Filed: Mar. 1, 1991

[30] Foreign Application Priority Data

Mar. 2, 1990 [JP] Japan .................................. 2-49580
Mar. 2, 1990 [JP] Japan .................................. 2-51947

[51] Int. Cl.$^5$ ..................... C08G 59/54; C08G 59/24; C08L 63/02; C08L 63/08
[52] U.S. Cl. ................... 523/404; 523/414; 528/111
[58] Field of Search ............... 528/111; 523/404, 414

[56] References Cited

U.S. PATENT DOCUMENTS

| | | | |
|---|---|---|---|
| 4,116,900 | 9/1978 | Belanger | 523/404 |
| 4,152,285 | 1/1979 | Thomassen | |
| 4,274,989 | 6/1981 | Tominaga | 523/415 |
| 4,514,467 | 4/1985 | Riemer et al. | 532/414 |
| 4,713,406 | 12/1987 | Schupp et al. | 523/414 |
| 5,089,542 | 2/1992 | Nishida | 523/404 |
| 5,091,446 | 2/1992 | Nishida | 523/414 |
| 5,096,984 | 3/1992 | Nishida | 523/404 |

FOREIGN PATENT DOCUMENTS 0301433 1/1989 European Pat. Off.
0356970 3/1990 European Pat. Off.

Primary Examiner—John C. Bleutge
Assistant Examiner—D. R. Wilson
Attorney, Agent, or Firm—Wenderoth, Lind & Ponack

[57] ABSTRACT

A coating resin composition composed mainly of an epoxy resin derivative obtained by reacting an amine compound containing hydroxyl groups, one secondary amino group and an amide group in the molecule with an epoxy group of an epoxy resin. The resin composition can be used alone, or in combination with an epoxy resin containing, per molecule, on the average at least 2 epoxy functional groups each comprising an epoxy groups directly bound to an alicyclic ring and/or bridged alicyclic ring. The resin is useful in a cationically electrodepositable paint.

27 Claims, No Drawings

COATING RESIN COMPOSITION

This invention relates to a novel resin composition for a paint, and more specifically to a resin composition having improved smoothness of a coated surface, bath stability and water dispersibility, and useful in a cationically electrodepositable paint.

Further, this invention relates to a resin composition for a cationically electrodepositable paint which is, when conjointly used with a curing agent, excellent in water dispersibility, stability and curability as well as in smoothness, adhesion, weatherability and low-temperature curability of a coated film.

Heretofore, as a resin for a cationically electrodepositable paint, (i) a polyamine resin such as an amine-added epoxide resin, e.g. an adduct of a polyepoxide and a secondary amine such as diethanolamine or ethylethanolamine has been used in most cases. This is crosslink-cured by an ester exchange reaction and/or an amide exchange reaction and/or an urethane exchange reaction and/or an urea exchange reaction and/or an etherification reaction with a terminal double bond to form an electrodeposition coated film. However, smoothness of a coated surface is not enough; in order to improve this, it has been required to lower the molecular weight of the adduct or to introduce a soft component that gives an effect of plasticity.

Nevertheless, when the molecular weight of the adduct is lowered, dispersion stability in water is decreased. When an external plastic component (e.g. a polyether polyol) is mixed to introduce the soft component, water dispersibility of the adduct is decreased. Meanwhile, when a polyfunctional soft component (e.g. sorbitol polyglycidyl ether) is chemically bound, the water dispersion is itself highly viscous, making it hard to smooth the coated surface. Even if a difunctional soft component (e.g. polypropylene glycol diglycidyl ether) is chemically bound, water dispersibility is decreased.

Moreover, (ii) an adduct of a polyepoxide and a secondary mono- or poly-amine containing a ketiminated primary amino group is known as a resin for a cationically electrodepositable paint (see, for example, U.S. Pat. No. 4,017,438). Said adduct is good in water dispersibility, but does not have sufficient smoothness in respect to the coated surface.

A blocked polyisocyanate compound is widely used as a curing agent of these resins for the cationically electrodepositable paint, but suffers varied problems, and there has been a strong demand to eliminate the same. Namely, regarding the adduct (i), it is difficult to meet both the water dispersibility and the corrosion resistance at the same time. Meanwhile, regarding the adduct (ii), especially when using a blocked polyisocyanate compound (curing agent) containing a blocked isocyanate functional group having low-temperature dissociation property and/or a blocked isocyanate functional group containing an active double bond (e.g. an isocyanate blocked with hydroxyethyl acrylate), storage (or bath) stability is poor because an active hydrogen-containing cationic group is present in the adduct (ii), and besides water dispersibility is not enough.

In addition, a resin composition for a cationically electrodepositable paint has serious substantial drawbacks that a temperature at which to start curing is high (usually above 170° C.); when an organotin compound is used as a curing catalyst to lower the temperature at which to start curing, said compound poisons an exhaust gas combustion catalyst of a baking furnace; and when heating is conducted at a high temperature to cure a coated film, the blocked isocyanate is heat decomposed so that gum and soot are generated, and a top coat film causes yellowing, bleeding and impediment of curing, notably decreases weatherability and tends to whiten. It has been long demanded to remedy these drawbacks as well.

The present inventors proposed beforehand a resin composition for a cationically electrodepositable paint by using a certain specific polyfunctional polymer as a curing agent, said resin composition being excellent in bath stability and curability without decreasing corrosion resistance, being able to remedy the aforesaid various drawbacks given by the organotin compound and the blocked polyisocyanate compound, having excellent adhesion because strain owing to volume shrinkage does not occur, remarkably improving weatherability of a coated film and being excellent in low-temperature curability (see EP-A 0356970 and U.S. patent application Ser. No. 07/401,138).

However, when said resin composition was subjected to a salt dip test at 50° C. of a film coated on an untreated steel plate, decrease in dispersibility of a cationic group was observed and there was a fear that dispersibility of an emulsion might be decreased.

Resins for an electrodepositable paint utilizing self crosslink-curability by a ring opening reaction between epoxy groups without the use of a curing agent have been hitherto known as proposed in e.g. GB 1,306,101-2, GB 1,327,071, GB 1,327,071 and U.S. Pat. No. 3,686,202. However, said resins cannot give bath stability of an electrodepositable paint and curability of a coated film at the same time. For example, among these resins, the most common glycidyl ether-type polyepoxy compound is excellent in curability but poor in bath stability.

This invention relates to a resin composition for a paint, and more specifically to a resin for a cationically electrodepositable paint that remedies the drawbacks of the resins for the cationically electro-depositable paint for example, the adducts (I) and (ii)) and even when conjointly used with the various curing agents, does not give the aforesaid drawbacks.

Under the aforesaid circumstances, the present inventors have made extensive studies to provide a coating resin composition excellent in smoothness of a coated surface, storage (or bath) stability and water dispersibility and especially useful in a cationically electro-depositable paint without the decrease in corrosion resistance, and consequently discovered that the above object can be achieved upon using as a film-forming resin an epoxy resin derivative obtained by reacting an amine compound containing hydroxyl groups, secondary amino groups and amide groups in a molecule with epoxy groups of an epoxy resin.

They have further discovered that by using the above epoxy resin derivative in combination with a specific polyfunctional polymer, there can be obtained, without decreasing corrosion resistance of a coated film, a film-forming resin composition for a cationically electrodepositable paint, which composition is excellent in water dispersiblity, bath stability and curability, can eliminate the aforesaid various drawbacks given by the use of the organotin compound and the blocked polyisocyanate compound, is excellent in adhesion because strain by volume shrinkage does not occur, remarkably improves weatherability of a coated film, has excellent low-temperature curability, can pass an untreated salt dip test and has excellent smoothness of a coated surface. Thus, in one aspect of this invention, there is provided a coating resin composition composed mainly of an epoxy resin derivative obtained by reacting an amine compound containing hydroxyl groups, secondary amino groups and amide groups in a molecule with an epoxy group of an epoxy resin.

In another aspect of this invention, there is provided a resin composition for a cationically electro-depositable paint, said composition comprising as principal components (a) an epoxy resin derivative obtained by reacting an amine compound containing hydroxyl groups, secondary amino groups and groups in a molecule with an epoxy groups of an epoxy resin, and (b) an epoxy resin containing, per molecule, on the average at least 2 epoxy functional groups each comprising an epoxy group directly bound to an alicyclic ring and/or a bridged alicyclic ring.

An electro-deposition coated film formed with the resin composition for the cationically electro-depositable paint in this invention is cured at a temperature of about 250° C. or lower. Especially when a compound containing a metal such as lead, zirconium, cobalt, aluminum, manganese, copper, zinc, iron, chromium or nickel is blended as a catalyst either singly or in combination, it can be cured even by heating at a low temperature of about 70° to about 160° C. Said curing presumably occurs such that the epoxy group contained in the epoxy resin (B) is reacted with the hydroxyl group (preferably, a primary hydroxyl group) of the resin (A) and besides the epoxy groups of the resin (B) are reacted to form ether linkages and cause crosslink-curing.

Accordingly, the resin composition for the cationically electro-depositable paint in this invention possesses advantages that said composition can be cured at a low temperature of 160° C. or less without the use of a tin catalyst; as the blocked isocyanate compound or its derivatives may not be used, the aforesaid various drawbacks provided by using same can be eliminated; because volume shrinkage owing to heat decomposition does not occur, good adhesion is exhibited; since an aromatic urethane bond or an aromatic urea bond is not introduced into crosslink, weatherability is little impaired; corrosion resistance and curability of the electro-deposition coated film are excellent; electro-deposition bath stability is good; because an amine compound, especially a compound of formula (I) to be described later is used as a cationizing agent, emulsion stability is good; smoothness of a coated surface is good; and excellent corrosion resistance is also shown in a salt dip test at 50° C. of a film coated on an untreated plate.

The resin composition provided by this invention will be described in more detail below.

(A) EPOXY RESIN DERIVATIVE

The epoxy resin derivative which is a main component of the coating resin composition in this invention is obtained, for example, by reacting an amine compound (A-1) containing hydroxyl groups, secondary amino groups and amide groups in a molecule with an epoxy group of an epoxy rein (A-2).

The amine compound (A-1) is a compound containing hydroxyl groups, preferably primary hydroxyl groups, secondary amino groups and amide groups in a molecule at the same time. Specifically, it is a compound represented by formula (I),

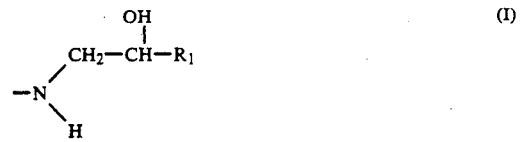

wherein n is an integer of 1 to 6, preferably 1 to 3, $R_1$ denotes a hydrogen atom, a methyl group or an ethyl group, and $R_2$ denotes a hydrocarbon group containing 4 to 36, preferably 8 to 24, more preferably 12 to 20 carbon atoms which group may contain a hydroxyl group and/or a polymerizable unsaturated group.

In formula (I), the hydrocarbon group indicated at $R_2$ includes a linear aliphatic hydrocarbon group, a branched aliphatic hydrocarbon group and an aliphatic hydrocarbon group that may optionally contain an alicyclic ring in a chain. Said aliphatic hydrocarbon group may optionally contain at least 1, preferably 1 to 3 hydroxyl groups as a substituent and/or at least 1, preferably 1 to 3 polymerizable double bonds in a chain. Such hydrocarbon group is a residue of an organic monocarboxylic acid of formula $R_2$—COOH (III) in a reaction scheme A to be shown later. Concrete examples of the monocarboxylic acid include caprylic acid, capric acid, lauric acid, myristic acid, palmitic acid, stearic acid, oleic acid, ricinoleic acid, linoleic acid, linolenic acid, eleostearic acid, 12-hydroxystearic acid and behenic acid. Of these, stearic acid, oleic acid, linoleic acid and 12-hydroxystearic acid are especially preferable.

The amine compound of formula (I) can be produced, as shown in the following reaction scheme A, by adding an organic monocarboxylic acid (III) containing 5 to 37 carbon atoms to a N-hydroxyalkylalkylenediamine compound (II) at an approximately equimolar ratio.

Reaction Scheme A

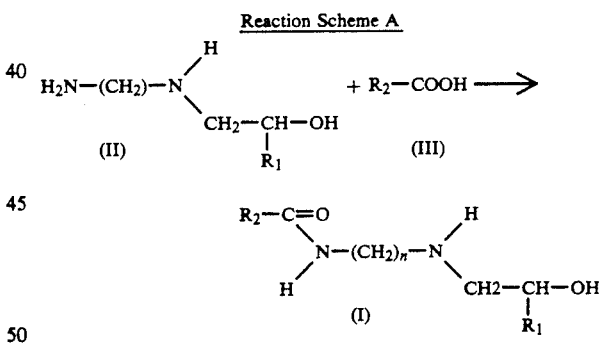

wherein $R_1$, $R_2$ and n are as defined above.

Desirable examples of the diamine compound (II) used in this reaction include hydroxyethylaminoethylamine, N-hydroxyethylpropylenediamine, N-hydroxyethylbutylenediamine, N-hydroxyethylpentylenediamine, N-hydroxyethylhexylenediamine, N-(2-hydroxy)-propylethylenediamine, N-(2-hydroxy)propylpropylenediamine, N-(2-hydroxy)propylbutylenediamine, N-(2-hydroxy)propylpentylenediamine, and N-(2-hydroxy)propylhexylenediamine. Among them, hydroxyethylaminoethylamine and N-hydroxyethylpropylenediamine are preferable.

Examples of the monocarboxylic acid (III) include mixed fatty acids such as a coconut oil fatty acid, a castor oil fatty acid, a rice bran oil fatty acid, a soybean oil fatty acid, a tall oil fatty acid, a dehydrated castor oil fatty acid, a safflower oil fatty acid, a linseed oil fatty acid, and a tung oil fatty acid, caprylic acid, capric acid, lauric acid, myristic acid, palmitic acid, stearic acid, oleic acid, ricinoleic acid, linoleic acid, linolenic acid, eleostearic acid, 12-hydroxystearic acid, and behenic acid. Of these, the tall oil fatty acid, stearic acid, oleic acid, linoleic acid and 12-hydroxystearic acid are especially preferable.

The equimolar adduct of the N-hydroxyalkylalkylenediamine (II) and the monocarboxylic acid (III) is formed by mixing both the components at a nearly equimolar ratio, removing a prescribed amount of a reaction water using an organic solvent such as toluene or methyl isobutyl ketone and removing the remaining organic solvent by a reduced pressure method.

The content of the hydroxyl groups in the amine compound (A-1) is usually 44 to 350, preferably 60 to 230, more preferably 100 to 200, calculated as a hydroxyl value. The content of the secondary amino groups is usually 88 to 350, preferably 120 to 230, more preferably 120 to 200, calculated as an amine value. A solidification point (according to a differential scanning calorimetry) is usually 100° C. or lower, preferably 85° C. or lower. The content of the amide groups is usually approximately the same (mols) as the content of the secondary amino groups.

As the epoxy resin (A-2) reacting with the amine compound (A-1), a polyepoxide compound containing on the average at least 2, preferably 2 to 30, more preferably 2 to 15 1,2-epoxy groups

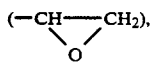

and having a number average molecular weight of at least 200, preferably 400 to 4,000 and more preferably 800 to 2,000, is suitable. As the polyepoxide compound, compounds known per se are available. For example, a polyphenol polyglycidyl ether resulting from reaction of a polyphenol and epichlorohydrin in the presence of an alkali is available. Typical examples of such polyepoxide compound include polyphenol glycidyl ethers such as bis(4-hydroxyphenyl)-2,2-propane, bis(4-hydroxyphenyl)-1,1-ethane, bis(4-hydroxyphenyl)-methane, 4,4'-dihydroxydiphenyl ether, 4,4'-dihydroxydiphenylsulfone, phenolic novolak and cresol novolak, and their polymerized products.

In the aforesaid polyepoxide compound, a polyphenol polyglycidyl ether having a number average molecular weight of at least about 380, preferably about 800 to about 2,000 and an epoxy equivalent of 190 to 2,000, preferably about 400 to 1,000 is especially preferable for high corrosion resistance. Most preferable is a polyepoxide compound represented by formula,

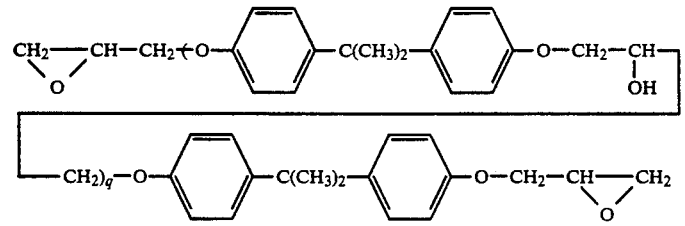

wherein q is 0 to 7, especially 0 to 4.

The epoxy resin derivative (A) can be formed by reacting the amine compound (A-1) with the epoxy resin (A-2). The reaction is presumably conducted, as shown in the following reaction scheme B, between the secondary amino group of the amine compound (A-1) and the epoxy group of the epoxy resin (A-2).

Reaction Scheme B

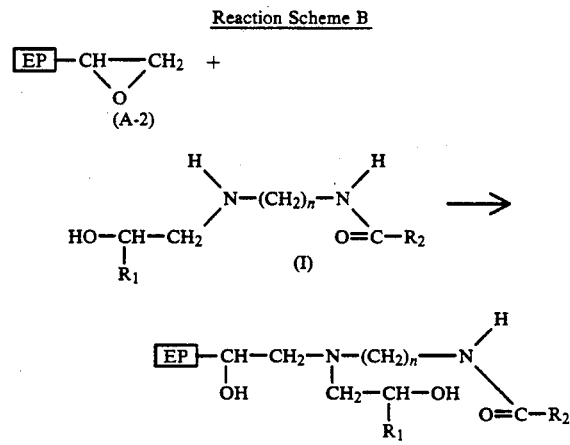

wherein [EP] denotes a skeletal portion of an epoxy resin )provided for simplicity, only 1 epoxy group is shown in the above reaction scheme, but at least one other epoxy group is bound to [EP]), and $R_1$, $R_2$ and n are as defined above.

The reaction of the epoxy resin (A-2) and the amine compound (A-1) proceeds by mere heating at a temperature of usually 50° to 140° C., preferably 70° to 120° C., and an alcoholic, ketonic or ethereal organic solvent may be used if required. A reaction ratio of the epoxy resin (A-2) and the amine compound (A-1) is not critical but can optionally be selected. In order to avoid gelation by an unreacted amino group or an epoxy group, it is advisable that an epoxy group/amino group equivalent ratio is 2/1 to 1/1, especially 1.5/1 to 1.05/1. When said ratio is outside the above range, it is advisable that part of the 1,2-epoxy group is blocked by previously reacting it with another reagent.

The amine compound of formula (I) contains a hydrocarbon group ($R_2$) having 4 or more carbon atoms. Since this moiety acts as a plastic component, another plastic component is substantially unnecessary. However, when better smoothness of a coated surface is required, it is possible to use an epoxy compound instead of or conjointly with the aforesaid polyepoxide compound. Examples of the epoxy compound (A-2) include polyglycidyl ethers of alicyclic polyols such as bis(4-hydroxycyclohexyl)-2,2-propane and bis(4-hydroxycyclohexyl)-methane, polyglycidyl esters of polycarboxylic acids such as terephthalic acid and tetrahydrophthalic acid, and an epoxidized 1,2-polybutadiene/glycidyl (meth)acrylate copolymer. Moreover, the above polyepoxide compound may partially be reacted with a polyol such as polycaprolactonediol or polypropylene glycol, a polyether polyol, a polyester polyol, a polyamideamine such as dimeric acid polyamide, a polycarboxylic acid such as a carboxyl-terminated acrylonitrile/butadiene copolymer, or a polyisocyanate. It may further be graft-polymerized with delta-4-caprolactone or an acrylic monomer.

The epoxy resin derivative (A) can further be modified to adjust hydrophilic nature (solubility or dispersibility in water) and ameliorate smoothness of a coated surface and physical properties of a coated film.

Modification Method 1)

Basicity and hydrophilic nature (water solubility or dispersibility) can be adjusted by reaction with an amine-type reactant containing active hydrogen and an amino group but free from an amide group. Examples of the amine-type reagent include primary amines such as methylamine, n- or iso-propylamine, monoethanolamine, ethylamine and n- or iso-propanolamine; secondary amines such as diethanolamine, diethylamine, N-ethylethanolamine, di-n- or di-iso-propanolamine and N-methylethanolamine; and polyamines such as ethylenediamine, diethylenetriamine, hydroxyethylaminoethylamine, ethyl aminoethylamine, methylaminopropylamine, dimethylaminoethylamine and dimethylaminopropylamine. Moreover, basic compounds such as ammonia, formaldehydeoxazolidine, hydrazine, hydroxyethylhydrazine and N-hydroxyethylimidazoline are also available.

Modification Method 2)

Basicity and hydrophilic nature of the resin derivative (A) may be adjusted by previously protonating an active hydrogen-free amine-type reagent and reacting the protonated reagent with an epoxy group to form a quaternary salt. Examples of the above reagent include tertiary amines such as triethylamine, triethanolamine, N,N-dimethylethanolamine, N-methyldiethanolamine, N,N-diethylethanolamine and N-ethyldiethanolamine.

Other than the amine compound, a salt of a sulfide such as diethyl sulfide, diphenyl sulfide, tetramethylene sulfide or thiodiethanol, and boric acid, carbonic acid or an organocarboxylic acid may be reacted with the epoxy group to form a tertiary sulfonium salt.

Moreover, a salt of triethylphosphine, phenyldimethylphosphine, diphenylmethylphosphine or triphenylphosphine and the above acid may be reacted with the epoxy group to form a quaternary phosphonium salt.

Modification Method 3)

Smoothness of a coated film of the resin derivative may be adjusted by reaction with a reagent (a monocarboxylic acid, a monophenol or a monoalcohol). Examples of the reagent used in this case include 2-ethylhexanoic acid, linoreic acid, nonylphenol and 2-ethylhexanol.

Modification Method 4)

Properties of a coated film can be modified by modifying the resin derivative via reaction with at least one type selected from a polyester, a polyether, a polyurethane and a polybutadiene containing a hydroxyl group, a carboxyl group and an amino group. Examples of the modifier used in this case include polycaprolactonediol, polypropylene glycol, dimeric acid polyamide, and a carboxyl-containing acrylonitrile/butadiene copolymer.

It is advisable that the above-described modification methods 1) to 4) are carried out previous to the reaction between the epoxy resin (A-2) and the amine compound (A-1); said methods may be conducted either simultaneously with or after said reaction.

The amount of the reagent or the modifier used to modify the epoxy resin is not particularly limited unless impairing the properties of the epoxy resin itself. The reagent or modifier/epoxy resin (A-2) ratio is usually not more than 1, preferably not more than 1/5.

The epoxy resin derivative (A) produced as described above has itself film formability at room temperature or under heating and can be used as a main component in a coating resin composition or a resin composition for paint.

On that occasion, to impart heat crosslink-curability to the composition, (i) a crosslinkable functional group capable of reacting with a hydroxyl group is introduced into a skeleton of the epoxy resin derivative (A) to give said derivative intermolecular crosslink-ability or (ii) an external curing agent having a crosslinkable functional group can be blended.

Examples of the crosslinkable functional group that can be introduced into the epoxy resin derivative (A) to give the intermolecular crosslinkability in (1) above include a blocked isocyanate group, a beta-hydroxy ester group, an alpha,beta-unsaturated carbonyl group, a N-methylol group and an epoxy group. From the aspects of low-temperature curability and bath stability, it is advisable that an isocyanage group blocked with a blocking agent having low-temperature dissociation property, a functional group having an active double bond (e.g. an isocyanate blocked with hydroxyethyl acrylate or N-methoxybutylacrylamide) or an epoxy group (e.g. a compound with an epoxy group directly bound to an alicyclic skeleton (including a bridged structure), EHPE-3150—a tradename for a product of Daicel Chemical Industries, Ltd.) is introduced as a crosslinkable functional group.

Examples of the external curing agent in (ii) above include compounds having at least 2 crosslinkable groups shown above in a molecule, such as blocked polyisocyanate compounds (including those showing low-temperature dissociation property and having an active double bond), polycarboxylic acid beta-hydroxyethyl esters, malonic ester derivatives, methylolated melamines, methylolated ureas, and the above epoxy group-containing alicyclic compounds.

When the epoxy resin derivative (A) is used as a coating resin composition, it is usually convenient that said derivative is dissolved or dispersed in water.

The epoxy resin derivative (A) can be solubilized or dispersed in water by, for example, protonating the tertiary amino group of the epoxy resin derivative with a water-soluble organocarboxylic acid such as formic acid, acetic acid or lactic acid. The amount (neutralization value) of the acid used in the protonation cannot strictly be defined, but it is usually about 5 to 40, especially preferably 10 to 20 KOH mg per gram of the resin solids content.

The coating resin composition containing the epoxy resin derivative (A) as the main component can contain, if required, a coloring pigment, an anticorrosive pigment, an extender pigment, a metallic pigment, an organic solvent, a curing catalyst and a surface active agent.

The coating resin composition can be coated by a coating method known per se, such as dip coating, spray coating, brushing, etc. Cationic electrodeposition coating is especially preferable.

A method and a device for electrodeposition coating can be a method and a device known per se in cathodical electro-deposition coating. In that case, it is advisable that a product being coated is used as a cathode and a stainless steel or carbon plate as an anode. The electrodeposition coating conditions are not particularly limited. Usually, a bath temperature is 20° to 30° C., a voltage 100 to 400 V (preferably 200 to 300 V), a current density 0.01 to 3 A/dM², a current passage time 1 to 5 minutes, an electrode area ratio (A/C) 2/1 to ½, and a distance between electrodes 10 to 100 cm respectively. Moreover, electro-deposition is conducted under stirring.

The coated film deposited on the product being coated in the cathode can be rinsed, and then based at about 140 to 200° C. for curing.

In still another aspect of this invention, the epoxy resin derivative (A) is combined with a specific epoxy resin (B) to be described later to form a resin composition for a cationically electro-depositable paint which is excellent in safety and curability as well as in adhesion, weatherability and low-temperature curability of a coated film.

When the epoxy resin derivative (A) is used in such resin composition for the cationically electro-depositable paint, the hydroxyl groups of the epoxy resin derivative (A) are hydroxyl groups introduced from the amine compound (A-1), primary hydroxyl groups which can be introduced from alkanolamines as the cationizing agent, ring-opened caprolactones that may be introduced into epoxide compounds, and polyols, and secondary hydroxyl groups of the epoxy resin (A-2). Of these, the primary hydroxyl groups introduced from the amine compounds of formula (I) with $R_1$=hydrogen atom and the alkanolamines shown in the modification method 1) are preferable because crosslink-curing reactivity by later is excellent.

The content of the hydroxyl groups in the epoxy resin derivative (A) is usually 20 to 5,000, preferably 100 to 1,000, calculated as a hydroxyl equivalent, from the aspect of crosslink-curing reactivity with the epoxy group contained in the epoxy resin (B) to be described later. Especially preferable is that the primary hydroxyl equivalent is 200 to 1,000. The content of the cationic groups is preferably higher than the lower limit necessary to stably disperse the epoxy resin derivative (A) in an aqueous medium. It is advisable that the total amount of the cationizing agent introduced from the amine compound (A-1) and the other cationizing agent is usually 3 to 200, preferably 10 to 80, more preferably 20 to 60, calculated as an amine value KOH(mg/g-solids content)]. However, even if the cationic group content is less than 3, it is possible to use it after making it an aqueous dispersion by the use of a surface active agent; in this case, however, it is desirable to adjust the cationic group so as to make the pH of the aqueous dispersed composition, usually 4 to 9, more preferably 6 to 7.

The epoxy resin derivative (A) used in the present invention has hydroxyl groups and cationic groups and is desirably free from free epoxy groups as a rule.

(B) EPOXY RESIN

Next, an explanation will be made with reference to the epoxy resin (B) used in admixture with said epoxy resin derivative (A) as a curing agent.

Said epoxy resin (B) which may be referred to hereinafter as "the curing resin (B)"] is a curing agent for forming a crosslinked paint film mainly by an etherification reaction with the epoxy resin derivative (A) as mentioned above, which contains at least 2, preferably at least 3, specified "epoxy functional groups" on average in one molecule.

Namely, said epoxy functional group in the curing resin (B) comprises an epoxy group directly bonded to an alicyclic ring and/or a bridged alicyclic ring in which said alicyclic ring is a 4-10 member, preferably 5-6 member saturated carbon monocyclic or polycyclic ring, while said bridged alicyclic ring contains bridges (endomethylene, endethylene, etc.) of a straight chain (linear) or branched $C_{1-6}$ (preferably $C_{1-4}$) alkylene group (for example, —CH₂—, —CH₂CH₂—, —CH(CH₃)—, —CH₂(CH₃)CH₂—, —C(CH₃)₂—, —CH(C , etc.) between 2 carbon atoms constituting said monocyclic or polycyclic ring.

On the other hand, an epoxy group

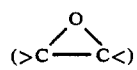

is important in that one of the carbon atoms in said epoxy group is directly bonded to the cyclic carbon atom (or atoms) of said alicyclic ring or said bridged alicyclic ring [see, for example, the following formulae (IV) and (V)], or the two carbon atoms of said epoxy group are common with the two adjoining carbon atoms constituting the ring in said alicyclic ring or said bridged alicyclic ring [see, for example, the following formulae (VII) and (VI)].

Specific examples of such epoxy functional group are represented by the following formulae (IV) to (VII).

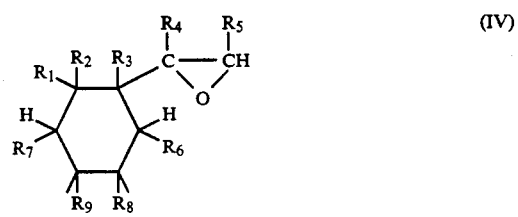

(IV)

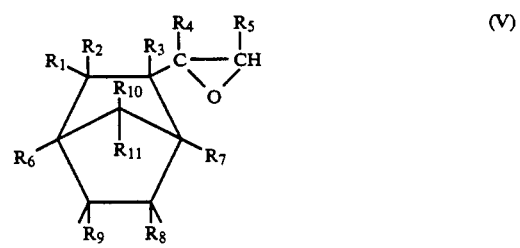

(V)

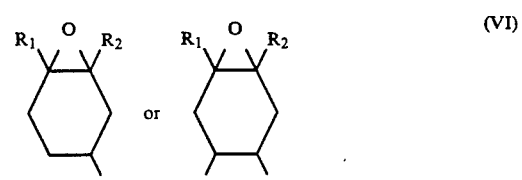

(VI)

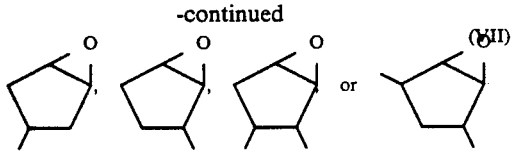

wherein $R_1$, $R_2$, $R_3$, $R_5$, $R_6$, $R_7$, $R_{10}$ and $R_{11}$ each denote H, $CH_3$ or $C_2H_5$, while $R_4$, $R_8$ and $R_9$ each denote H or $CH_3$.

The epoxy resin (B) used in the present invention may have at least 2, preferably at least 3, more preferably at least 4, epoxy functional groups selected from said formulae (IV) to (VII) on average in one molecule. For example, the epoxy resin (B) may have at least one kind of the epoxy functional group represented by said formula (IV) or (V), or may have at least one kind of the epoxy functional group represented by said formula (VI) or (VII) in one molecule. Furthermore, the epoxy resin (B) may have at least one kind of the epoxy functional group represented by said formula (IV) or (V) and at least one kind of the epoxy functional group represented by said formula (VI) or (VII) within one and the same molecule or in different molecules.

The epoxy functional group represented by said formula (IV) or (VI) are preferable, and especially, an epoxy functional group represented by the following formula (VIII)

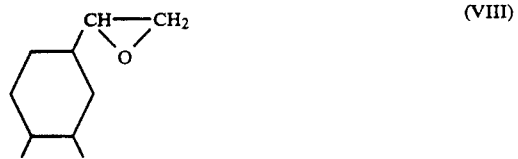

and an epoxy functional group represented by the following formula (IX) are preferable.

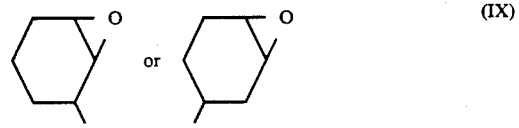

Additionally, the epoxy equivalent and the molecular weight of the epoxy resin (B) used in the present invention are not strictly restricted, but are changeable according to a process for the production thereof and the use of the end resin composition. But, generally speaking, the epoxy equivalent may be within the range of usually 100 to 2,000, preferably 150 to 500, more preferably 150 to 250.

And it is proper that the number average molecular weight is within the range of usually 400 to 100,000, preferably 700 to 50,000, more preferably 700 to 30,000.

The epoxy resin [the curing resin (B)] having at least 2 such epoxy functional groups in one molecule is described in literatures such as, for example, Japanese Patent Publication No. 8016/1981 as well as Japanese Laid-Open Patent Publications Nos. 47365/1982, 66675/1985, 221121/1968 and 234028/ 1988, and what is known per se may be used.

Or said epoxy resin (B) having said epoxy functional groups is obtained by processes known per se. The main processes for producing said epoxy resin (B) will be enumerated hereinbelow, but the enumerated processes are not limitative.

A first process for the production:

A process for producing an epoxy resin having at least 2 epoxy functional groups in one molecule which comprises epoxidizing part of carbon-carbon double bonds of an alicyclic compound having said at least 2 carbon-carbon double bonds in one molecule, subjecting the resulting epoxy groups to ring-opening polymerization, and thereafter epoxidizing said double bonds remaining in the resulting polymer.

A second process for the production:

A process for subjecting an alicyclic compound having at least 2 epoxy groups in the same molecule to ring-opening polymerization to such an extent as may not eliminate all of said epoxy groups on the basis of said epoxy groups.

A third process for the production:

A process for polymerizing a compound having an epoxy functional group and a polymerizable unsaturated bond in the same molecule.

A more specific explanation will be made with reference to these processes for the production hereinbelow.

THE FIRST PROCESS FOR THE PRODUCTION

This process comprises epoxidizing part of carbon-carbon double bonds (a partial epoxidation product) contained in an alicyclic compound having at least 2 carbon-carbon double bonds in one molecule [hereinafter referred to as "the alicyclic compound (a)"], obtaining a ring-opened polymer of said partial epoxidation product by ring-opening polymerization of the resulting epoxy groups, and thereafter epoxidizing part or whole of said double bonds remaining in said polymer to thereby obtain a curing resin (B).

The alicyclic compound (a) is a compound having a structure of an alicyclic ring or a bridged alicyclic ring mentioned above and at least 2 carbon-carbon double bonds, existing between 2 adjoining carbon atoms constituting the ring structure or between the other carbon atoms being directly bonded to said ring structure.

The alicyclic compound (a) may also be obtained by heating, for example, a conjugated diene compound by a known method. As such conjugated diene compound, an aliphatic or alicyclic compound having 4 to 30 carbon atoms and having at least 1 pair, preferably 1 to 5 pairs of conjugated double bonds in one molecule is suitable.

Specific examples of such conjugated diene compound include butadiene, isoprene, pirylene, 1,3-hexadiene, 2,4-hexadiene, 2,4-heptadiene, 2-methyl-6-methylene-2,7-octadiene, 2,6-dimethyl-1,5,7-octatriene, cyclopentadiene, cyclohexadiene, 4-ethyl-2-methylcyclosopropylcyclopentadiene, 1,2,3,4-tetraphenylcyclopentadiene, 1,2,4-triphenylcyclopentadiene, 1,4-diphenylcyclopentadiene, 1,3-octachloropentadiene, hexachlorocyclopentadiene, 5,5-diethoxy-1,2,3,4-tetrachlorocyclopentadiene, 1,2,3,4,5-pentachlorocyclopentadiene, 1,2,3,4-cyclooctadiene, 1,3,5-cyclooctatriene, 1,3,6-cyclooctatriene, cyclooctatetraene, chlorocyclooctatetraene, bromocyclooctatetraene and 5-cyclohexylidenecyclopentadiene. These conjugated diene compounds may be used singly or in combination, respectively.

As required, when a conjugated diene compound under heating is reacted in the presence of a Ziegler catalyst, the alicyclic compound (a) is obtained. This reaction under heating may be carried out by a method known per se, for example, by a method disclosed in Japanese Laid-Open Patent Publication No. 102643/1974.

Typical examples of the so obtained alicyclic compound (a) are as follows.

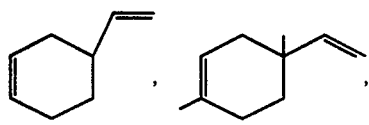

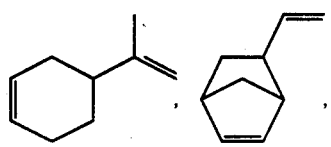

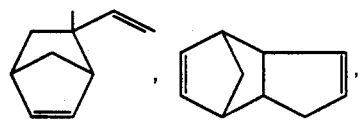

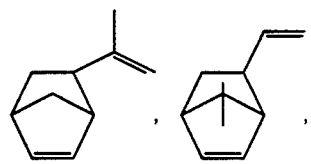

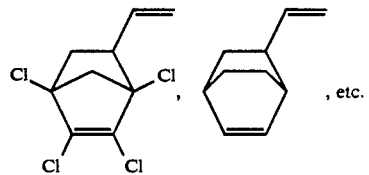
, etc.

Of the aforesaid conjugated diene compounds, alicyclic compounds such as cyclopentadiene, cyclohexadiene and 4-ethyl-2-methylcyclopentadiene; and such compounds as sylvestrene, 2,8(9)-p-menthadiene, pyronene, 1,3-dimethyl-1-ethyl-3,5-cyclohexadiene, terpinene, phellandrene, dipentene, iso-limonene and limonene have already structures of the alicyclic compound (a). Therefore, these compounds may be used per se without being subjected to said reaction under heating.

At first, part of (at least 2) carbon-carbon double bonds contained in the alicyclic compound (a) is modified to epoxy groups with a peroxide and so forth (partial epoxidation). The partial epoxidation product is obtained by modifying part of a plurality of double bonds contained in said alicyclic compound (a) to epoxy groups. Specific examples of such partial epoxidation product are as follows.

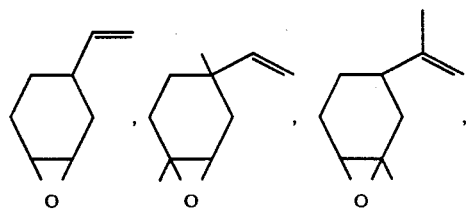

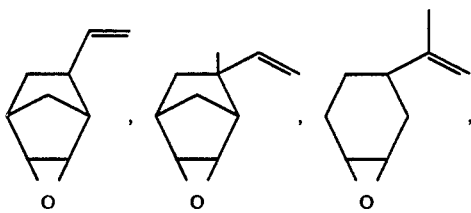

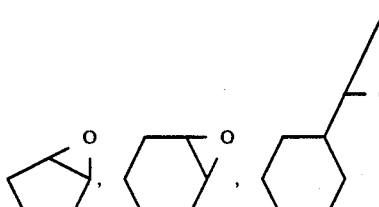

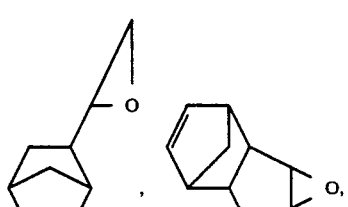

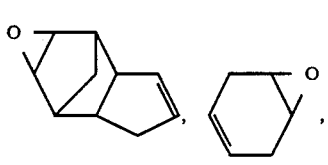

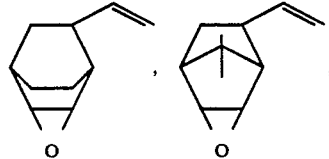

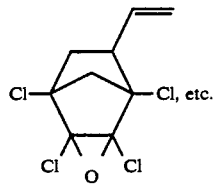

Naturally available epoxy carene may also be used as a partial epoxidation product.

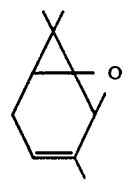

A partial epoxidation product has at least 1 epoxy group and at least 1 carbon-carbon double bond in one molecule, and said double bond is required to exist between 2 adjoining carbon atoms constituting the ring or between the other carbon atoms directly bonded to said ring.

Next, based on epoxy groups in this partial epoxidation product, ring-opening polymerization is carried out to obtain a polymer of the alicyclic compound (a). It is preferable to use a polymerization initiator for this ring-opening polymerization, and the terminal of the end product of the curing resin (B), a residue X by the initiator component(s) may be bonded, where X is a residue of an organic compound having active hydrogen. As an organic compound having active hydrogen which is a precursor of X, there may be cited, for example, alcohols, phenols, carboxylic acids, amines and thiols. Of these, as the alcohols, either one or monohydric alcohols or di- or higher polyhydric alcohls will do. Specific examples of the alcohols include aliphatic monohydric alcohols such as methanol, ethanol, propanol, butanol, pentanol, hexanol and octanol; an aromatic monohydric alcohol such as benzyl alcohol; and polyhydric alcohols such as ethylene glycol, diethylene glycol, triethylene glycol, polyethylene glycol, propylene glycol, dipropylene glycol, 1,3-butanediol, 1,4-butanediol, pentanediol, 1,6-hexanediol, neopentyl glycol, hydroxypivalic acid neopentyl glycol ester, cyclohexane dimethanol, glycerin, diglycerin, diglycerin, polyglycerin, trimethylol propane, trimethylol ethane, pentaerythritol and dipentaerythritol.

Specific examples of the phenols include phenol, cresol, catechol, pyrogallol, hydroquinone, hydroquinone monomethylether, bisphenol A, bisphenol F, 4,4'-dihydroxybenzophenone, bisphenol S, phenol resin and cresol novolak resin.

As the carboxylic acids, there may be illustrated formic acid, acetic acid, propionic acid, butyric acid, fatty acid of animal and vegetable oils; fumaric acid, maleic acid, adipic acid, dodecanoic diacid, trimellitic acid, pyromellitic acid, polyacrylic acid, phthalic acid, isophthalic acid and terephthalic acid, and further, a compound having both hydroxyl group and a carboxylic acid such as lactic acid, citric acid and hydroxycaproic acid may be used as well.

Besides, as the other compound having active hydrogen, a mixture of water and alkoxysilane such as tetramethyl silicate, tetraethyl silicate, methyltrimethoxysilane, methyltriethoxysilane, dimethyl dimethoxysilane and phenyl trimethoxysilane or silanol compounds of these; polyvinyl alcohol, a polyvinyl acetate partial hydrolyzed product, starch, cellulose, cellulose acetate, cellulose acetate butyrate, hydroxyethyl cellulose, acrylpolyol resin, styrene-allyl alcohol copolymer resin, styrene-maleic acid copolymer resin, alkyd resin, polyesterpolyol resin and polycaprolactonepolyol resin may be also used. Such compound may have an unsaturated double bond together with active hydrogen; further, said unsaturated double bond may be epoxidated. And a catalyst and a polymerization initiator may be the same like an alkoxy metal compound. Usually, the aforesaid organic compound having active hydrogen is used as a polymerization initiator, while the aforesaid partial epoxidation product such as, for example, 4-vinylcyclohexene-1-oxide, 4-vinylcyclo2,2,1)-3-methyl-4(or 5)-t-propenyl-1-cyclohexene oxide, 2,4- or 1,4-dimethyl-4-ethenyl-1-cyclohexene oxide, 4-vinylcyclo[2,2,1]-heptene-1-oxide (vinylnorbornene oxide) and 2-methyl-4-isopropanyl-cyclohexene oxide are used singly or in combination upon carrying out ring-opening polymerization. At this time, it is also possible to carry out ring-opening polymerization in the co-presence of the other epoxy compound but belonging to said partial epoxidation product. As the other copolymerizable epoxy compound, any compound will do so long as it has an epoxy group, but suitable examples of such other copolymerizable epoxy compound include an oxide of an unsaturated compound such as ethylene oxide, propylene oxide, butylene oxide and styrene oxide; a glycidyl ether compound such as allylglycidyl ether, 2-ethylhexylglycidyl ether, methylglycidyl ether, butylglycidyl ether and phenylglycidyl ether; unsaturated organic carboxylic acid glycidyl ester compound such as acrylic acid and methacrylic acid; and an alicyclic oxiran group-containing vinyl monomer such as 3,4-epoxycyclohexyl methyl (meth)acrylate.

The aforesaid ring-opened polymer is obtained by ring-opening polymerizing epoxy groups contained in a partial epoxidation product alone or as required in the other epoxy compound made to be co-present with said partial epoxidation product to form an ether bond. The proportion of the other epoxy compound in a ring-opened polymer may be optionally selected in accordance with the object, but specifically, it is desirable to select said epoxy compound within such a range of proportion that said compound may have at least 2, preferably at least 3, more preferably at least 4, of one or more kinds of said structural formulae (IV) to (VII) on average per molecule of the resulting ring-opened polymer. It is preferable that the number average molecular weight of the so obtained (co)polymer is within the range of usually from 400 to 100,000, especially from 700 to 50,000, more especially 700 to 30,000.

It is generally preferable to carry out a ring-opening polymerization reaction in the presence of a catalyst.

Specific examples of the catalyst that can be used include amines such as methyl amine, ethyl amine, propyl amine and piperazine; organic bases such as pyridines and imidazoles; organic acids such as formic acid, acetic acid and propionic acid; inorganic acids such as sulfuric acid and hydrochloric acid; alkali metal alcoholates such as sodium methylate; alkalis such as KOH and NaOH; Lewis acid or its complexes such as $BF_3$, $ZnCl_2$, $AlCl_3$ and $SnCl_4$; and organometallic compounds such as triethyl aluminum, aluminum acetyl acetonate, titanium acetyl acetonate and diethyl zinc.

These catalysts may be used in amounts within the range of generally 0.001 to 10% by weight, preferably 0.1 to 5% by weight based on the reactant. The ring-opening polymerization temperature is within the range of generally about $-70°$ to about $200°$ C., preferably about $-30°$ to about $100°$ C. The reaction may be carried out in the presence of a solvent, and it is preferable to use an ordinary organic solvent not having active hydrogen as a solvent.

In the ring-opened polymer, there are double bonds derived from the alicyclic compound (a), and the epoxy resin (B) is obtained by epoxidating part or whole of said double bonds. Epoxidation of the double bonds may be carried out by using an epoxidation agent such as, for example, peroxy acids and hydroperoxides. Whether a solvent should be used or not and the reaction temperature in the epoxidation reaction may be properly adjusted according to the apparatus used and the physical properties of the starting material. Depending on the conditions of the epoxidation reaction, simultaneous with epoxidation of the double bonds in the ring-opened polymer as a starting material, a side reaction occurs and the modified substituent may be contained in the skeleton of the epoxy resin sometimes. As such modified substituent, when, for example, peracetic acid is used as the epoxidation agent, a substituent of the following structure may be cited, which is considered to be attributable to reaction of the produced epoxy group with the by-produced acetic acid.

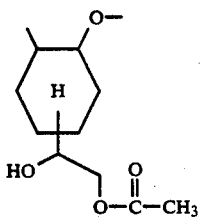

The ratio at which these substituents are contained in said skeleton is determined according to the kind of the epoxidation agent, the molar ratio of the epoxidation agent to the unsaturated bond and the reaction conditions.

The epoxy equivalent of the so obtained epoxy resin (B) is preferably within the range of generally 100 to 2,000, especially 150 to 500, more especially 150 to 250.

As such epoxy resin (B), what is commercially available may also be used, and as such merchandise, for example, EHPE-3150, EHPE-3100 and EHPE-1150 (tradenames for products of Daicel Chemical Industries, Ltd.) may be cited. These are epoxy resins of the following structural formula having cyclohexene skeletons using 4-vinylcyclohexene-1-oxide as a partial epoxidation product for their production.

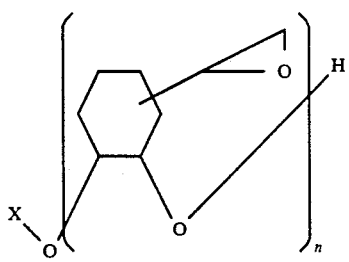

wherein n is at least 2, preferably at least 3, more preferably at least 4.

THE SECOND PROCESS FOR THE PRODUCTION

According to this process, the objective epoxy resin is obtained by, for example, epoxidizing at least 2 of the double bonds contained in said alicyclic compound (a), and thereafter subjecting said compound (a) to ring-opening polymerization in such a manner as to retain the resulting epoxy groups.

As said epoxidation product having at least 2 epoxy groups on average per molecule, the following monocyclic or condensed ring-type compounds may be shown as typical examples.

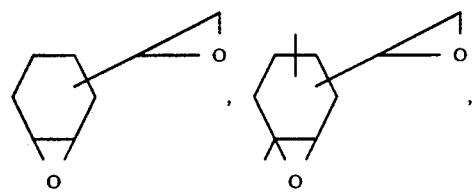

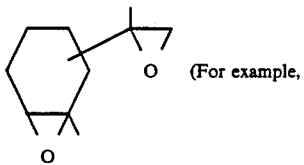

(For example, a product under a tradename of "Celoxide" of Daicel Chemical Industries, Ltd. may be

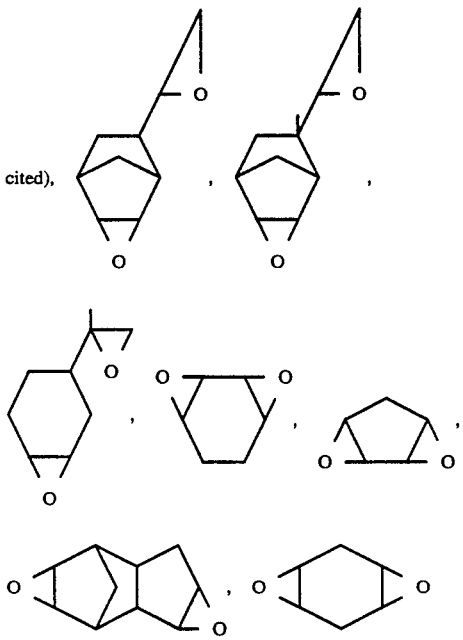

Specifically, at least one kind of said epoxy compound is subjected to ring-opening polymerization, as required in the presence of a polymerization initiator and a catalyst in the same way as in the first process for the production mentioned above and the reaction is suspended at the predetermined reaction stage in which epoxy groups are remaining to thereby obtain the epoxy resin (B). For suspending the reaction, optional means such as dilution with a solvent and cooling may be used. In this process for the production, said other epoxy compound may be copolymerized as in said first process for the production as well.

The so obtained curing resin (B) may be an epoxy resin having at least one kind of the epoxy functional group shown by said formula (IV) or (V) and at least one kind of the epoxy functional group shown by said formula (VI) or (VII) in the same molecule or different molecules.

The so obtained ring-opened polymer the curing resin (B)] preferably has a number average molecular weight within the range of generally 400 to 100,000, especially 700 to 50,000 and conveniently has an epoxy equivalent within the range of generally 100 to 2,000, especially 150 to 500, more especially 150 to 250.

THE THIRD PROCESS FOR THE PRODUCTION

Examples of a compound having at least one epoxy functional group and a polymerizable unsaturated bond in the same molecule (which may be hereinafter referred to as "a polymerizable epoxy monomer") are compounds represented by the following general formulae ① to ⑫.
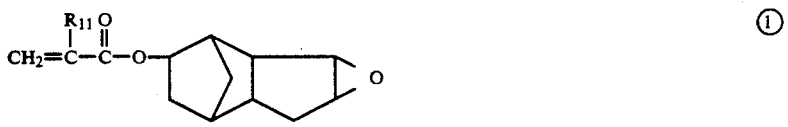
①
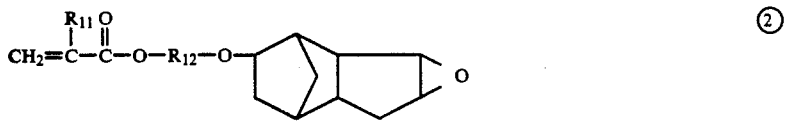
②
③
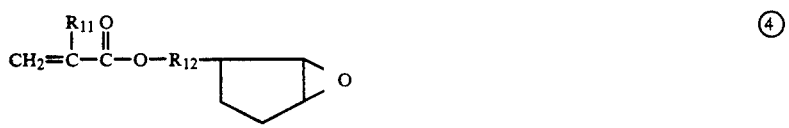
④
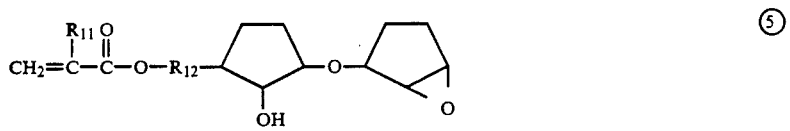
⑤
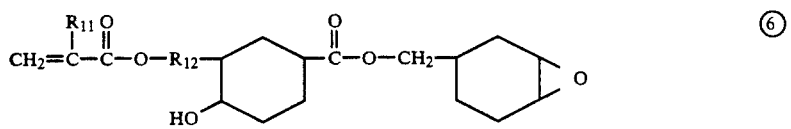
⑥
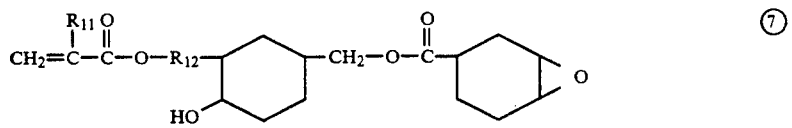
⑦
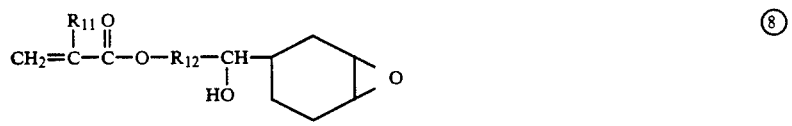
⑧
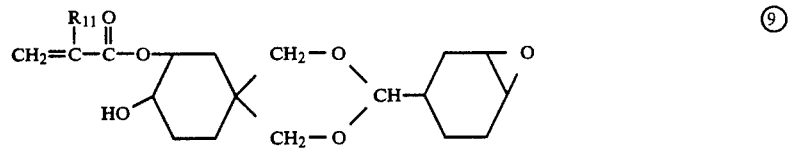
⑨
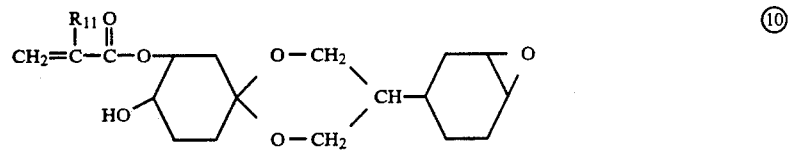
⑩
⑪

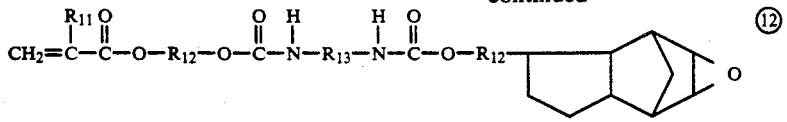

In said general formulae $R_{11}$ represents a hydrogen atom or a methyl group, $R_{12}$ represents a divalent aliphatic saturated hydrocarbon group having 1 to 6 carbon atoms, and $R_{13}$ represents a divalent hydrocarbon group having 1 to 10 carbon atoms.

In the aforesaid copolymerizable epoxy monomers, as a divalent aliphatic saturated hydrocarbon group having 1 to 6 carbon atoms represented by $R_{12}$, there may be cited a straight chain linear or branched chain alkylene group such as, for example, methylene, ethylene, propylene, tetramethylene, ethylethylene, pentamethylene and hexamethylene. As a divalent hydrocarbon group having 1 to 10 carbon atoms represented by $R_{13}$, there may be cited, for example, methylene, ethylene, propylene, tetramethylene, ethylethylene, pentamethylene, hexamethylene, polymethylene, phenylene,

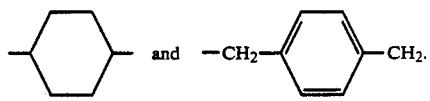

Specific examples of the polymerizable epoxy monomers represented by the aforesaid general formulae ① to ⑫ include 3,4-epoxycyclohexylmethyl acrylate and 3,4-epoxyhexylmethyl methacrylate. They are commercially available, for example, under tradenames of "METHB" and "AETHB", both products of Daicel Chemical Industries, Ltd. They have the epoxy functional group represented by said formula (IV) or (V). Further, 4-vinylcyclohexene oxide may also be used as a polymerizable epoxy monomer.

The epoxy resin (B) may be produced by polymerizing one kind or at least two kinds of monomers selected from these polymerizable epoxy monomers, and at this time, it is also possible to copolymerize the other polymerizable unsaturated monomer.

As the other polymerizable unsaturated monomer, it may be selected from a broad range according to the properties desired of the resulting (co)polymer. Typical examples of such other polymerizable unsaturated monomer include the following compounds.

(a) Acrylic acid or methacrylic acid esters: for example, alkyl esters having 1 to 18 carbon atoms of acrylic acid or methacrylic acid such as methyl acrylate, ethyl acrylate, propyl acrylate, isopropyl acrylate, butyl acrylate, hexyl acrylate, octyl acrylate, lauryl acrylate, methyl methacrylate, ethyl methacrylate, propyl methacrylate, isopropyl methacrylate, butyl methacrylate, hexyl methacrylate, octyl methacrylate and lauryl methacrylate; alkoxyalkyl esters having 2 to 18 carbon atoms of acrylic acid or methacrylic acid such as methoxybutyl acrylate, methoxybutyl methacrylate, methoxyethyl acrylate, methoxyethyl methacrylate, ethoxybutyl acrylate and ethoxybutyl methacrylate; alkenyl esters having 2 to 8 carbon atoms of acrylic acid or methacrylic acid such as allyl acrylate and allyl methacrylate; hydroxyalkyl esters having 2 to 8 carbon atoms of acrylic acid or methacrylic acid such as 2-hydroxyethyl acrylate, 2-hydroxyethyl methacrylate, hydroxypropyl acrylate and hydroxypropyl methacrylate; and alkenyloxyalkyl esters having 3 to 18 carbon atoms of acrylic acid or methacrylic acid such as allyloxyethyl acrylate and allyloxyethyl methacrylate.

(b) Vinyl aromatic compounds: for example, styrene, alpha-methyl styrene, vinyl toluene and p-chlorostyrene.

(c) Polyolefin type compounds, for example, butadiene, isoprene and chloroprene.

(d) Others: acrylonitrile, methacrylonitrile, methylisopropenyl ketone, vinyl acetate, VEOBA monomer (a product of Shell Chemicals), vinyl propionate, vinyl pivalate and a compound having a polycaprolactam chain (for example, FM-3X monomer, a trade name of a product of Daicel Chemical Industries, Ltd.)

The ratio of the polymerizable epoxy monomer to the other polymerizable unsaturated monomer may be optionally selected according to the object, within such a range as to enable the epoxy resin (B) obtained by these copolymerization reactions to contain at least 2, preferably at least 3, more preferably at least 4, epoxy functional groups on average in one molecule. But in order to invest the resulting polymer with sufficient curability, it is especially preferable to make the content of the polymerizable epoxy monomer in the solids content of said epoxy resin (B) within the range of 5 to 100% by more preferably 20 to 100% by weight.

Said third process for the production of the epoxy resin (B) may be carried out in the same manner as the polymerization reaction of ordinary acryl or vinyl resin monomers. As one of such polymerization reactions, a process which comprises dissolving or dispersing the respective monomer components in an organic solvent, and heating the resulting solution or dispersion at a temperature of about 60° to 180° C. with stirring in the presence of a radical polymerization initiator, may be shown. The reaction time may be normally about 1 to 10 hours. As the organic solvent, alcohol solvents, ether solvents, ester solvents and hydrocarbon solvents may be used. When the hydrocarbon solvent is used, it is preferable to use another cosolvent together with it from the stand-point of the solubility. Further, all of usually used radical polymerization initiators may be used. Specific examples of such radical initiator include peroxides such as benzoyl peroxide and t-butyl peroxy-2-ethyl hexanoate; and azo compounds such as azobisisobutyronitrile and azobisdimethylvaleronitrile.

It is preferable that the epoxy resin (B) obtained by said third process for the production has a number average molecular weight within the range of generally about 3,000 to about 100,000, especially 4,000 to 10,000.

Of the aforesaid curing resins (B), the epoxy resin is most suitable having at least 3 epoxy functional groups, more preferably at least 4 such groups, most preferably at least 5 such groups, on average per molecule, having an epoxy equivalent within the range of preferably 100 to 2,000, more preferably 150 to 500, especially preferably 150 to 250, and a number average molecular weight within the range of preferably 400 to 100,000, more preferably 700 to 50,000, especially preferably 750 to 30,000.

RESIN COMPOSITION FOR A CATIONICALLY ELECTRODEPOSITABLE PAINT

A resin composition for a cationically electro-depositable paint can be prepared by using the aforesaid epoxy resin derivative (A) and epoxy resin (B) in combination.

The amount to use the curing resin (B) is properly changeable according to the kind of the epoxy resin derivative (A) used and within the range from the minimum amount enough to cure the resulting paint film thermally to the maximum amount which does not hurt the bath stability, but generally it is desirably within such a range that the weight ratio of the solids content of the curing resin (B) to the epoxy resin derivative (A) becomes 0.2 to 1.0, especially 0.25 to 0.85, more desirably 0.25 to 0.65.

The resin composition for a cathodically electrodepositable paint of the present invention may contain an adduct of the curing resin (B) and the epoxy resin derivative (A).

Thus, the composition comprising the epoxy resin derivative (A) and the curing resin (B) may be used as a resin composition for a cathodically electrodepositable paint.

For preparing the resin composition for a cathodically electrodepositable paint of the present invention, for example, the epoxy resin derivative (A) and the curing resin (B) are mixed, and then the resulting mixture is stably dispersed in water. Then, as required, the resulting aqueous dispersion is blended with a color pigment such as carbon black, titanium white, white lead, lead oxide and red iron oxide; an extender pigment such as clay and talc; an anticorrosive pigment such as strontium chromate, lead chromate, basic lead chromate, red lead, lead silicate, basic lead silicate, lead phosphate, basic lead phosphate, lead tripolyphosphate, lead silicochromate, chrome yellow, lead cyanamide, calcium plumbate, lead suboxide, lead sulfate and basic lead sulfate; or further with other additives. As the other additives that can be blended, for example, a small amount of a dispersant or a nonionic surface active agent as a cissing preventing agent of the coated surface; and curing promotor may be cited.

Especially, for making an electrodeposited paint sufficiently curable at a low temperature of not more than 160° C., it is effective to add one kind or at least two kinds of metallic compound selected from among a lead compound, a zirconium compound, a cobalt compound, an aluminum compound, a manganese compound, a copper compound, a zinc compound, an iron compound, a chromium compound and a nickel compound as a catalyst.

Specific examples of these metal compounds include chelated compounds such as zirconium acetyl acetonate, cobalt acetyl acetonate, aluminum acetyl acetonate and manganese acetyl acetonate; a chelation reaction product of compounds having beta-hydroxyamino structures with lead oxide (II); and carboxylates such as lead 2-ethyl hexanoate, lead oenanthate, naphthex lead, lead octanoate, lead benzoate, lead acetate, lead lactate, lead formate, lead glycoate and octanoate zircinium.

Said metal compounds may be used in an amount calculated as a metal content based on the weight of the total solids content of the epoxy resin derivative (A) and the curing resin (B) of generally not more than 10% by weight, preferably not more than 5% by weight.

The thickness of a paint film obtained by electrodepositing the so prepared resin composition for a cathodically electrodepositable paint on a proper substrate is not strictly restricted; however, generally, the thickness within the range of 3 to 300 microns based on the cured paint film is suitable. The paint film can be cured with heating at a temperature of, for example, 70° to 250° C., preferably 120° to 160° C.

A method of forming an electrodeposited paint film on the substrate using the resin composition for a cathodically electrodepositable paint of the present invention is not particularly restricted, but ordinary conditions for cathodically electrodepositing may be used. For example, the epoxy resin derivative (A) and the epoxy curing resin (B) according to this invention are, as mentioned above, dispersed in water, the resulting aqueous dispersion is blended with, as required, pigments, a curing catalyst and other additives, further, the mixture is diluted to the concentration of the solids content of the bath within the range of 5 to 40% by weight, preferably 10 to 25% by weight, and the bath pH is adjusted within the range of 5 to 8, preferably 5.5 to 7. Next, using this electrodeposition bath, electrodeposition is carried out under the following conditions with, for example, a carbon plate (5 cm × 15 cm × 1 cm) being used as an anode and for example, a zinc phosphate-treated steel (5 cm × 15 cm × 0.7 mm) being used as a cathode.

Bath temperature: 20 to 35° C., preferably 25 to 30° C.
Direct current
Current density: 0.005 to 2 A/cm$^2$, preferably 0.01 to 1 A/cm$^2$
Voltage: 10 to 500 V, preferably 100 to 300 V
Power feeding time: 0.5 to 5 min., preferably 2 to 3 min.

After the electrodeposition coating, the coated product can be drawn up from the electrodeposition bath, and rinsed with water. The moisture contained in the electrodeposition coated film is removed by a drying means such as a heat, and the resulting product is then heat cured by heating as mentioned above.

In the epoxy resin derivative (A) in the coating resin composition of this invention, the tertiary amino group introduced from the amine compound (A-1) makes water dispersibility in low neutralization good, the hydrocarbon group containing 4 or more carbon atoms gives smoothness of a coated surface and an active hydrogen-containing cationic group is absent, so that even if conjointly using as a crosslinkable functional group an isocyanate group blocked with a blocking agent having low-temperature dissociation property or a functional group having an active double bond (e.g. an isocyanate group blocked with hydroxyethyl acrylate or N-methoxybutylacrylamide), a desirable cationically electro-depositable coating or aqueous coating resin composition can be provided without impairing stability.

The primary hydroxyl groups introduced from said amine can be reacted with functional groups capable of reacting with said hydroxyl groups without sacrificing corrosion resistance, making it possible to provide a cationically electrodepositable coating or an aqueous coating resin composition having good corrosion resistance.

The following Examples illustrate this invention more specifically. However, this invention is not limited thereto. Parts and percentages in said Examples are all by weight unless otherwise indicated.

I. PREPARATION EXAMPLES

(1) Amine Compound (A-1)

1) Amine Compound (A-1-1)

A reaction vessel fitted with a thermometer, a stirrer, a reflux condenser, and a water separator was charged with 285 parts of stearic acid, 104 parts of hydroxyethylaminoethylamine and 80 parts of toluene. With mixing and stirring, the mixture was progressively heated, and toluene was removed if required. While raising the temperature, 18 parts of a reaction water was removed by separation, and the remaining toluene was removed under reduced pressure to obtain an amine compound (A-1-1) having an amine value of 150, a hydroxyl value of 151 and a solidification point of 76° C.

2) Amine Compound (A-1-2)

A reaction vessel fitted with a thermometer, a stirrer, a reflux condenser, and a water separator was charged with 283 parts of a tall oil fatty acid, 104 parts of hydroxyethylaminoethylamine and 80 parts of toluene. With mixing and stirring, the mixture was progressively heated, and toluene was removed if required. While elevating the temperature, 18 parts of a reaction water was removed by separation, and the remaining toluene was then removed under reduced pressure to obtain an amine compound (A-1-2) having an amine value of 151, a hydroxyl value of 152 and a solidification point of 20° C. or lower.

3) Amine Compound (A-1-3)

A reaction vessel fitted with a thermometer, a stirrer, a reflux condenser, a water separator was charged with 300 parts of 12-hydroxystearic acid, 104 parts of hydroxyethylaminoethylamine and 80 parts of toluene. With mixing and stirring, the mixture was progressively heated, and toluene was removed if required. While elevating the temperature, 18 parts of a reaction water was removed by separation, and the remaining toluene was then removed under reduced pressure to obtain an amine compound (A-1-3) having an amine value of 148, a hydroxyl value of 149 and a solidification point of 69° C.

4) Partially Blocked Polyisocyanate Compound (B-NCO-1)

A reaction vessel fitted with a thermometer, a stirrer, a reflux condenser and a dropping funnel was charged with 222 parts of isophorone diisocyanate, 37 parts of methyl isobutyl ketone, 0.1 part of dibutyltin dilaurate and 1 part of hydroquinone monomethyl ether. Hydroxyethyl acrylate (116 parts) was added dropwise at 100° C., and the reaction was run until a NCO value reached 112 to obtain a partially blocked polyisocyanate compound (B-NCO-1).

5) Sample for Comparison

A reaction vessel fitted with a thermometer, a stirrer, a reflux condenser and a water separator was charged with 103 parts of diethylenetriamine and 314 parts of methyl isobutyl ketone. With mixing and stirring, the mixture was progressively heated. While raising the temperature, 36 parts of a reaction water was removed by separation to obtain a sample (1) for comparison.

(2) Curing Resin (B)

1) Curing Resin (B-1)

"EHPE.3150" [tradename for an epoxy resin having an epoxy equivalent of 175 to 195, a product of Daicel Chemical Industries, Ltd.] (32.6 parts) and 8.2 parts of propylene glycol monomethyl ether were dissolved under heating at 100° C. to obtain 40.8 parts of a curing resin (B-1) having a solids content of 80% and an epoxy equivalent of 190. Said curing resin had a number average molecular weight of about 1,500.

2) Curing Resin (B-2)

To a mixture of 136 parts of vinyl norbornene oxide, 124 parts of 4-vinylcyclohexene-1-oxide and 18 parts of trimethylol propane and 200 parts of a 10% ethyl acetate solution of $BF_3$-etherate were added dropwise at 50° C. over 4 hours to carry out ring-opening polymerization. The resultant ring-opened polymer was blended with ethyl acetate, washed with water. The ethyl acetate layer was concentrated, then 130 parts of ethyl acetate was added anew and dissolved, and 160 parts of peracetic acid was made into an ethyl acetate solution and added dropwise at 50° C. over 5 hours. The resultant mixture was matured for 2 hours to carry out an epoxidation reaction. After removing acetic acid, ethyl acetate and peracetic acid, the remaining epoxidation product was dissolved in 500 parts of ethyl acetate at 40° C., followed by washing with 250 parts of distilled water 4 times. Then ethyl acetate was removed, and the matured product was dissolved in 78 parts of propylene glycol monoethyl ether at 80° C. to obtain a curing resin (B-2) having a solids content of 80% and an epoxy equivalent of 202. Said curing resin had a number average molecular weight of about 1,300.

3) Curing Resin (B-3)

To a mixture of 304 parts of partially epoxidated lemonene (2-methyl-4-isopropenyl-1-cyclohexene oxide) and 18 parts of trimethylol propane, 200 parts of a 10% ethyl acetate solution of $BF_3$-etherate was added dropwise at 50° C. over 4 hours. The treatment thereafter was carried out as in the curing resin (B-2), and the matured product was dissolved in 80 parts of ethylene glycol monobutyl ether at 80° C. to obtain a curing resin (B-3) having a solids content of 80% and an epoxy equivalent of 205. Said curing resin had a number average molecular weight of about 1,000.

4) Curing Resin (B-4)

The process for producing a curing resin (B-2) was repeated except that 304 parts of 2,4- or 1,4-dimethyl-4-ethenyl-1-cyclohexane oxide was used to obtain a curing resin (B-4) having a solids content of 80% and an epoxy equivalent of 199. Said curing resin had a number average molecular weight of about 950.

5) Curing Resin (B-5)

To a mixture of 460 parts of "Celoxide 3000"

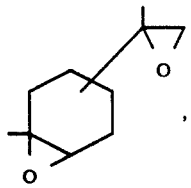

a tradename for a product of Daicel Chemical Industries, Ltd.], 0.3 part of aluminum acetyl acetonate and 5 parts of tetraethoxy silane, 0.1 part of distilled water were added, and the mixture was maintained at 80° C. for 1 hour and then reacted at 12° C. for 3 hours. Thereafter, to the reaction product was added 116 parts of ethylene glycol monobutyl ether to obtain a curing resin (B-5) having a solids content of 80% and an epoxy equivalent of 280. Said curing resin had a number average molecular weight of about 1,700.

6) Curing Resin (B-6)

A cyclopentadiene dimer (132 parts) was dissolved in 70 parts of ethyl acetate. To the resulting solution, 160 parts of peracetic acid as an ethyl acetate solution was added dropwise at 35° C. over 7 hours, and the mixture was further matured at 40° C. for 6 hours. After removal of acetic acid, ethyl acetate and peracetic acid, the matured product was dissolved at 40° C. in 500 parts of ethyl acetate, followed by washing with 250 parts of distilled water 5 times. Then ethyl acetate was removed and the matured product was dissolved at 80° C. in 43 parts of methylisobutyl ketone to obtain a compound (b) having a solids content of 80% and an epoxy equivalent of 90. 4-Vinylcyclohexene (94 parts) was dissolved in 75 parts of ethyl acetate. To the resulting solution, 160 parts of peracetic acid made into an ethyl acetate solution was added dropwise at 50° C. over 4 hours, and the mixture was further matured at 50° C. for 2 hours. After removal of acetic acid, ethyl acetate and peracetic acid, the matured product was dissolved in 500 parts of ethyl acetate at 40° C., followed by washing with 250 parts of distilled water 5 times. Then ethyl acetate was removed, and the matured product was dissolved at 80° C. in 32 parts of methylisobutyl ketone to obtain a compound (c) having a solids content of 80% and an epoxy equivalent of 65. To a mixture of 225 parts of the compound (b) and 163 parts of the compound (c), 0.2 part of aluminum acetyl acetonate and 10 parts of trimethylol propane were added, and the resulting mixture was maintained at 100° C. for 1 hour, and then reacted at 150° C. for 3 hours. Subsequently, 60 parts of ethylene glycol monobutyl ether was added to cool the system to thereby obtain a curing resin (B-6) having a solids content of 70% and an epoxy equivalent of 210. Said curing resin had a number average molecular weight of about 1,100.

7) Curing Resin (B-7)

Azobisdimethylvaleronitrile (2 parts) dissolved in 33.4 parts of METHB monomer (3,4-epoxycyclohexylmethyl methacrylate) was added dropwise to a mixed solvent of 10 parts of methyl isobutyl ketone and 10 parts of butyl cellosolve heated at 100° C. over 2 hours. The resulting mixture was matured for 1 hour, then heated to 125° C., at which temperature the matured mixture was further matured for 1 hour to obtain a curing resin (B-7) having a solids content of 60% and an epoxy equivalent of 196. Said curing resin had a number average molecular weight of about 10,000.

8) Curing Resin (B-8)

Azobisdimethylvaleronitrile (2.4 parts) dissolved in a mixture of 32.0 parts of an METHB monomer and 8.0 parts of hydroxyethyl acrylate was added dropwise to 24 parts of butyl cellosolve heated at 100° C. over 2 hours, and matured for 1 hour. Then the system was heated at 125° C., and again matured for 1 more hour to obtain a curing resin (B-8) having a solids content of 60% and an epoxy equivalent of 245. Said curing resin had a number average molecular weight of about 12,000.

9) Curing resin (B-9)

Azobisdimethylvaleronitrile (2.4 parts) dissolved in a mixture of 37 parts of 3,4-epoxycyclohexylmethyl acrylate and 3 parts of hydroxyethyl acrylate was treated in the same way as in the preceding process for the production of the curing resin (B-8) to obtain a curing resin (B-9) having a solids content of 60% and an epoxy equivalent of 200. Said curing resin had a number average molecular weight of about 15,000.

10) Curing Resin (B-10) for Comparison

A reaction vessel fitted with a thermometer, a stirrer and a reflux condenser was charged with 250 parts of 4,4-diphenylmethane diisocyanate and 150 parts of methyl ethyl ketone. After the temperature was elevated to 50° C., 348 parts of ethylene glycol mono-2-ethylhexyl ether was added dropwise. The temperature was raised to 80° C., and the reaction was carried out until a NCO value reached 0. There was obtained a curing resin (B-10).

(3) Pigment Pastes

1) Pigment Paste (P-1)

To the epoxy resin derivative [A-2] (12.5 parts) which will be described in Example 2 later was added 4.4 parts of 10% formic acid. Fifteen parts of deionized water was then added with stirring. Ten parts of titanium white, 10 parts of clay, 1 part of carbon and parts of basic lead silicate were further added to the mixture. The resulting mixture was dispersed in a ball mill for 24 hours and 11 parts of deionized water was further added to obtain a paste (P-1) having a solids content of 50%.

2) Pigment Paste for Comparison (P-2)

A pigment paste (P-2) was formed as in (P-1) except adding 1.5 parts of dibutyltin dilaurate.

II. EXAMPLES

Example 1

A reaction vessel fitted with a thermometer, a stirrer and a reflux condenser was charged with 988 parts of bisphenol A diglycidyl ether having an epoxy equivalent of about 190, 365 parts of bisphenol A and 10.5 parts of diethanolamine. The reaction was run at 120° C. until the epoxy equivalent reached 682 (a number average molecular weight 1,370). Then, the reaction mixture was diluted with 343 parts of ethylene glycol monobutyl ether and cooled. Subsequently, while keeping the temperature at 80° C., 126 parts of diethanolamine and 224 parts of the amine compound (A-1-1) were added. Until increase of viscosity stopped, the reaction was conducted. Thereafter, 228 parts of methyl isobutyl ketone was added to obtain an epoxy resin derivative (A-1) having a solids content of 75%, a primary hydroxyl equivalent of 535 and an amine value of 62.

Example 2

A reaction vessel fitted with a thermometer, a stirrer and a reflux condenser was charged with 988 parts of bisphenol A diglycidyl ether having an epoxy equivalent of about 190, 365 parts of bisphenol A and 10.5 parts of diethanolamine. The reaction was run at 120° C. until the epoxy equivalent reached 682 (a number average molecular weight 1,370). Then, the reaction mixture was diluted with 343 parts of ethylene glycol monobutyl ether and cooled. While keeping the temperature at 80° C., 126 parts of diethanolamine and 224 parts of the amine compound (A-1-2) were added, and the reaction was conducted until increase of viscosity stopped. Subsequently, 228 parts of methyl isobutyl ketone was added to obtain an epoxy resin derivative (A-2) having a solids content of 75%, a primary hydroxyl equivalent of 535 and an amine value of 62.

Example 3

A reaction vessel fitted with a thermometer, a stirrer and a reflux condenser was charged with 912 parts of bisphenol A diglycidyl ether having an epoxy equivalent of about 190, 365 parts of bisphenol A, 136 parts of polypropylene glycol diglycidyl ether having an epoxy equivalent of 340 and 10.5 parts of diethanolamine. The reaction was run at 120° C. until the epoxy equivalent reached 712 (a number average molecular weight 1,440). Thereafter, the reaction mixture was diluted with 355 parts of ethylene glycol monobutyl ether and cooled. While keeping the temperature at 80° C., 126 parts of diethanolamine and 227 parts of the amine compound (A-1-3) were added, and the reaction was carried out until increase of viscosity stopped. Thereafter, 237 parts of methyl isobutyl ketone was added to afford an epoxy resin derivative (A-3) having a solids content of 75%, a primary hydroxyl equivalent of 557 and an amine value of 60.

Example 4

A reaction vessel fitted with a thermometer, a stirrer, a reflux condenser and a dropping funnel was charged with 988 parts of bisphenol A diglycidyl ether having an epoxy equivalent of about 190, 365 parts of bisphenol A and 10.5 parts of diethanolamine. The reaction was run at 120° C. until the epoxy equivalent reached 682 (a number average molecular weight 1370). Then, the reaction mixture was diluted with 236 parts of methyl isobutyl ketone and cooled. While keeping the temperature at 80° C., 126 parts of diethanolamine and 224 parts of the amino compound (A-1-1) were added, and the reaction was conducted until increase of viscosity stopped. Subsequently, 376 parts of B-NCO-1 was added dropwise, it was confirmed by IR that the NCO residue disappeared, and 410 parts of ethylene glycol monobutyl ether was added to obtain an epoxy resin derivative (A-4) having a solids content of 75%, a primary hydroxyl equivalent of 641 and an amine value of 52.

Comparative Example 1

A reaction vessel fitted with a thermometer, a stirrer and a reflux condenser was charged with 912 parts of bisphenol A diglycidyl ether having an epoxy equivalent of about 190, 365 parts of bisphenol A, 136 parts of polypropylene glycol diglycidyl ether having an epoxy equivalent of 340 and 10.5 parts of diethanolamine. The reaction was run at 120° C. until the epoxy equivalent reached 712. Subsequently, the reaction mixture was diluted with 355 parts of ethylene glycol monobutyl ether and cooled. While maintaining the temperature at 80° C., 189 parts of diethanolamine was added. Until increase of viscosity stopped, the reaction was carried out. Then, 183 parts of methyl isobutyl ketone was added to obtain a resin (1) for comparison.

Comparative Example 2

A reaction vessel fitted with a thermometer, a stirrer and a reflux condenser was charged with 988 parts of bisphenol A diglycidyl ether having an epoxy equivalent of about 190, 365 parts of bisphenol A and 10.5 parts of diethanolamine. The reaction was run at 120° C. until the epoxy equivalent reached 682. Then, the reaction mixture was diluted with 343 parts of ethylene glycol monobutyl ether and cooled. While maintaining the temperature at 80° C., 168 parts of diethanolamine and 76 parts of the sample (1) for comparison. The reaction was conducted until increase of viscosity stopped. There obtain a resin (2) for comparison.

Comparative Example 3

A reaction vessel fitted with a thermometer, a stirrer and a reflux condenser was charged with 912 parts of bisphenol A diglycidyl ether having an epoxy equivalent of about 190, 365 parts of bisphenol A, 136 parts of polypropylene glycol diglycidyl ether having an epoxy equivalent of 340 and 10.5 parts of diethanolamine. The reaction was run at 120° C. until the epoxy equivalent reached 712. Then, the reaction mixture was diluted with 329 parts of ethylene glycol monobutyl ether and cooled. While keeping the temperature at 80° C., 168 parts of diethanolamine and 76.3 parts of the sample (1) for comparison were added. The reaction was conducted until increase of viscosity stopped, and 196 parts of methyl isobutyl ketone was added to obtain a resin (3) for comparison.

Comparative Example 4

A reaction vessel fitted with a thermometer, a stirrer, a reflux condenser and a dropping funnel was charged with 912 parts of bisphenol A diglycidyl ether having an epoxy equivalent of about 190, 365 parts of bisphenol A, 136 parts of polypropylene glycol diglycidyl ether having an epoxy equivalent of 340 and 10.5 parts of diethanolamine. The reaction was conducted at 120° C. until the epoxy equivalent reached 712. Thereafter, the reaction mixture was diluted with 233 parts of methyl isobutyl ketone and cooled. While keeping the temperature at 80° C., 168 parts of diethanolamine and 76.3 parts of the sample (1) for comparison were added, and the reaction was carried out until increase of viscosity stopped. Thereafter, 376 parts of (B-NCO-1) was added dropwise, it was confirmed by IR that the NCO residue disappeared, and 367 parts of ethylene glycol monobutyl ether was added to obtain a resin (4) for comparison.

Example 5

One hundred parts of the epoxy resin derivative (A-1) (a resin solids content 75%), 25 parts of methyl ethyl ketoximate blocked 4,4′-diphenylmethane diisocyanate and 1 part of polypropylene glycol (PP-4000, a tradename for a product of Sanyo Chemical Industries Ltd.) were mixed, and 1.70 parts of acetic acid was then added. While heating the mixture at 60° C. with stirring, deionized water was gradually added and the mixture was dispersed in water to obtain a stable emulsion having a resin solids content of 30%. A particle diameter of the emulsion was 0.2 micron.

To this were added 3 parts of basic lead silicate, 13 parts of titanium white, 0.3 part of carbon black, 3 parts of clay, 2 parts of dibutyltin oxide and 1 part of a nonionic surface active agent 142B (a tradename for a product of Daiichi Kogyo Seiyaku Co., Ltd.). The pigments were dispersed with a ball mill until a particle diameter reached 10 microns or less. The pigment dispersion was further diluted with deionized water until the solids content of 20% was reached. After open stirring at 28° C. for 1 day, the resulting product was electrodeposited on a zinc phosphate treated steel plate (Bt #3080) at a bath temperature of 28° C. and a voltage of 250 V for 3 minutes, and baked at 160° C. for 20 minutes to afford a coated film having a thickness of about 20 microns and showing excellent smoothness.

After the paint was further stirred at 28° C. for 2 weeks in a closed state, the same electrodeposition was conducted to obtain a coated film having a thickness of about 20 microns and showing excellent smoothness.

Example 6

Eighty five parts of the epoxy resin derivative (A-2) (a resin solids content 75%), 25 parts of the blocked isocyanate in Example 5 and 1 part of polypropylene glycol (PP-4000, a tradename for a product of Sanyo Kasei Kogyo K.K.) were mixed, and 1.70 parts of acetic acid was then added. While heating the mixture at 60° C. with stirring, deionized water was gradually added and the mixture was dispersed in water to obtain a stable emulsion having a resin solids content of 30%. A particle diameter of the emulsion was 0.15 micron.

To 15 parts of the epoxy resin derivative (A-2) (a resin solids content 75%) were added 6 parts of ethylene glycol monobutyl ether, 4 parts of basic lead silicate, 13 parts of titanium white, 0.3 part of carbon black, 3 parts of clay and 1 part of a nonionic surface active agent 142B (a tradename for a product of Daiichi Kogyo Seiyaku K.K.). The pigments were dispersed with a ball mill until a particle diameter of 10 microns or less was reached. The resulting pigment dispersion was mixed with the above emulsion, and the mixture was diluted to a solids content of 20% with deionized water. After open-stirring at 28° C. for 1 day, the resulting mixture was electrodeposited on a zinc phosphate-treated steel plate (Bt #3080) at a bath temperature of 28° C. and a voltage of 250 V for 3 minutes, and baked at 160° C. for 20 minutes to obtain a coated film having a thickness of about 20 microns and showing excellent smoothness.

After the paint was further stirred at 28° C. for 2 weeks in a closed state, the same electrodeposition was carried out to obtain a coated film having a thickness of about 20 microns and showing excellent smoothness.

Example 7

One hundred parts of the epoxy resin derivative (A-3) (a resin solids content 75%), 25 parts of ethylene glycol mono-2-ethylhexyl ether blocked 4,4'-diphenylmethane diisocyanate and 1 part of polypropylene glycol (PP-4000, a tradename for a product of Sanyo Kasei Kogyo K.K.) were mixed, and 1.70 parts of acetic acid was then added. While heating the mixture at 60° C. with stirring, deionized water was gradually added and the mixture was dispersed in water to obtain a stable emulsion having a resin solids content of 30%. A particle diameter of the emulsion was 0.15 micron.

To this were added 3 parts of basic lead silicate, 13 parts of titanium white, 0.3 part of carbon black, 3 parts of clay, 2 parts of dibutyltin oxide and 1 part of a nonionic surface active agent 142B (a tradename for a product of Daiichi Kogyo Seiyaku K.K.). The pigments were dispersed with a ball mill until a particle diameter of 10 microns or less was reached. The pigment dispersion was diluted to a solids content of 20% with deionized water. After open-stirring at 28° C. for 1 day, the pigment dispersion was electrodeposited on a zinc phosphate-treated steel plate (Bt #3080) at a bath temperature of 28° C. and a voltage of 250 V for 3 minutes, and baked at 160° C. for 20 minutes to afford a coated film having a thickness of about 25 microns and showing excellent smoothness.

After the paint was further stirred at 28° C. for 2 weeks in a closed state, the same electrodeposition was carried out to obtain a coated film having a thickness of about 25 microns and showing excellent smoothness.

Example 8

After 133 parts of the epoxy resin derivative (A-4) (a resin solids content 75%) and 1 part of polypropylene glycol (PP-4000, a tradename for a product of Sanyo Kasei Kogyo K.K.) were mixed, 1.70 parts of acetic acid was added. While heating the mixture at 60° C. with stirring, deionized water was gradually added and the mixture was dispersed in water to obtain a stable emulsion having a resin solids content of 30%. A particle diameter of the emulsion was 0.18 micron.

To this emulsion were added 3 parts of basic lead silicate, 13 parts of titanium white, 0.3 part of carbon black, 3 parts of clay, 2 parts of dibutyltin oxide and 1 part of a nonionic surface active agent 142B (a tradename for a product of Daiichi Kogyo Seiyaku K.K.). The pigments were dispersed with a ball mill until a particle diameter of 10 microns or less was reached. The pigment dispersion was further diluted to a solids content of 20% with deionized water. After open-stirring at 28° C. for 1 day, the resulting dispersion was electrodeposited on a zinc phosphate-treated steel plate (Bt #3080) at a bath temperature of 28° C. and a voltage of 250 V for 3 minutes, and baked at 160° C. for 20 minutes to obtain a coated film having a thickness of about 20 microns and showing excellent smoothness.

After the paint was further stirred at 28° C. for 2 weeks in a closed state, the same electrodeposition was carried out to obtain a coated film having a thickness of about 20 microns and showing excellent smoothness.

Comparative Example 5

One hundred parts of the resin (1) for comparison (a resin solids content 75%), 25 parts of ethylene glycol mono-2-ethylhexyl ether blocked 4,4'-diphenylmethane diisocyanate and 1 part of polypropylene glycol (PP-4000, a tradename for a product of Sanyo Kasei Kogyo K.K.) were mixed, and 1.70 parts of acetic acid was then added. While heating the mixture at 60° C. with stirring, deionized water was gradually added and the mixture was dispersed in water to form an emulsion having a resin solids content of 30%. A particle diameter of the emulsion was 0.6 micron or more. Therefore, when the amount of the acid was increased to 2.13 parts, a solution was formed. However, the emulsion was separated and sedimented at 30° C. in 1 week.

Comparative Example 6

One hundred parts of the resin (2) for comparison (a resin solids content 75%), 25 parts of ethylene glycol mono-2-ethylhexyl ether blocked 4,4'-diphenylmethane diisocyanate and 1 part of polypropylene glycol (PP-4000, a tradename for a product of Sanyo Kasei Kogyo K.K.) were mixed, and 1.70 parts of acetic acid was then added. While heating the mixture at 60° C. with stirring, deionized water was gradually added and the mixture was dispersed in water to produce an emulsion having a resin solids content of 30%. A particle diameter of the emulsion was however 0.2 micron.

To this emulsion were added 3 parts of basic lead silicate, 13 parts of titanium white, 0.3 part of carbon black, 3 parts of clay, 2 parts of dibutyltin oxide and 1 part of a nonionic surface active agent 142B (a tradename for a product of Daiichi Kogyo Seiyaku K.K.). The pigments were dispersed with a ball mill until a particle diameter of 10 microns or less was reached. The dispersion was further diluted to a solids content of 20% with deionized water. After open stirring at 28° C. for 1 day, the resulting product was electrodeposited on a zinc phosphate-treated steel plate (Bt #3080) at a bath temperature of 28° C. and a voltage of 250 V for 3 minutes, and baked at 160° C. for 20 minutes to obtain a coated film having a thickness of about 15 microns. However, it had a coated surface showing poor smoothness.

Comparative Example 7

Eighty five parts of the resin (3) for comparison (a resin solids content 75%), 25 parts of the blocked isocyanate in Example 5 and 1 part of polypropylene glycol (PP-4000, a tradename for a product of Sanyo Kasei Kogyo K.K.) were mixed, and 1.70 parts of acetic acid was added. While heating the mixture at 60° C. with stirring, deionized water was gradually added and the mixture was dispersed in water to obtain a stable emulsion having a resin solids content of 30%. A particle diameter of the emulsion was 0.15 micron.

To 15 parts of the resin (3) for comparison (a resin solids content 75%) were added 6 parts of ethylene glycol monobutyl ether, 4 parts of basic lead silicate, 3 parts of titanium white, 0.3 part of carbon black, 3 parts of clay and 1 part of a nonionic surface active agent 142B (a tradename for a product of Daiichi Kogyo K.K.). The pigments were dispersed with a ball mill until a particle diameter of 10 microns or less was reached. The resulting pigment dispersion was mixed with the above emulsion, and the mixture was further diluted to a solids content of 20% with deionized water. After open-stirring at 28° C. for 1 day, the resulting product was electrodeposited on a zinc phosphate-treated steel plate (Bt #3080) at a bath temperature of 28° C. and a voltage of 250 V for 3 minutes, and baked at 160° C. for 20 minutes to obtain a smooth coated film having a thickness of about 20 microns.

After this paint was further stirred at 28° C. for 2 weeks in a closed state, the same electrodeposition was carried out. Then, a coated surface having very poor smoothness was provided.

Comparative Example 8

The resin (4) for comparison (133 parts: a resin solids content 75%) and 1 part of polypropylene glycol (PP-4000, a tradename for a product of Sanyo Kasei Kogyo K.K.) were mixed, and 1.70 parts of acetic acid was then added. While heating the mixture at 60° C. with stirring, deionized water was gradually added, and the mixture was dispersed in water to obtain a stable emulsion having a resin solids content of 30%. A particle diameter of the emulsion was 0.18 micron.

To this emulsion were added 3 parts of basic lead silicate, 13 parts of titanium white, 0.3 part of carbon black, 3 parts of clay, 2 parts of dibutyltin oxide and 1 part of a nonionic surface active agent 142B (a tradename for a product of Daiichi Kogyo Seiyaku K.K.). The pigments were dispersed with a ball mill until a particle diameter of 10 microns or less was reached. Then, gelation occurred.

Comparative Example 9

Thirty nine parts of monoethanolamine was maintained in a reaction vessel at 60° C., and 100 parts of N,N-dimethylaminopropylacrylamide was added dropwise. The reaction was run at 60° C. for 5 hours to obtain a mono-ethanolamine adduct of N,N-dimethylaminopropylacrylamide.

Separately, 950 parts of bisphenol A diglycidyl ether having an epoxy equivalent of 190, 340 parts of propylene glycol diglycidyl ether having an epoxy equivalent of 340, 456 parts of bisphenol A and 21 parts of diethanolamine were charged and heated to 120° C. The reaction was conducted until an epoxy value reached 1.02 mmols/g. Subsequently, the reaction mixture was diluted with 656 parts of ethylene glycol monobutyl ether and cooled. While keeping the temperature at 100° C., 158 parts of diethanolamine and 43 parts of the monoethanolamine adduct of N,N-dimethylaminopropylacrylamide were added. The reaction was run until increase of viscosity stopped. There resulted a resin (5) for comparison having a resin solids content of 75%, a primary hydroxyl equivalent of 518 and an amine value of 54.

Examples 9 to 19 and Comparative Examples 10 to 12

Using the epoxy resin derivatives produced in Examples 1 to 3, the resin (5) for comparison produced in Comparative Example 9 and the curing resins produced in Preparation Examples, aqueous emulsions were formed to obtain the resin compositions for a cationically electrodepositable paint. The compositions and the amounts of the respective components of said resin compositions are shown in Table 1.

TABLE 1

| | Epoxy resin derivative (A) | Curing resin | 100% Formic acid | Lead octanoate | Deionized water | Particle diameter of an emulsion ( ) |
|---|---|---|---|---|---|---|
| Example | | | | | | |
| 9 | A-1 87 | B-1 31 | 15 | 2.6 | 315 | 0.25 |
| 10 | A-1 87 | B-2 31 | 15 | 2.6 | 315 | 0.3 |
| 11 | A-1 87 | B-3 31 | 15 | 2.6 | 315 | 0.25 |
| 12 | A-1 87 | B-4 31 | 15 | 2.6 | 315 | 0.2 |
| 13 | A-1 87 | B-5 31 | 15 | 2.6 | 315 | 0.3 |
| 14 | A-1 87 | B-6 36 | 15 | 2.6 | 310 | 0.3 |

TABLE 1-continued

|   | Epoxy resin derivative (A) | Curing resin | 100% Formic acid | Lead octanoate | Deionized water | Particle diameter of an emulsion ( ) |
|---|---|---|---|---|---|---|
| 15 | A-1 87 | B-7 42 | 15 | 2.6 | 304 | 0.25 |
| 16 | A-1 87 | B-8 42 | 15 | 2.6 | 304 | 0.3 |
| 17 | A-1 87 | B-9 42 | 15 | 2.6 | 304 | 0.2 |
| 18 | A-2 87 | B-1 31 | 15 | 2.6 | 315 | 0.25 |
| 19 | A-3 87 | B-1 31 | 15 | 2.6 | 315 | 0.3 |
| Comparative Example |  |  |  |  |  |  |
| 10 | A-1 87 | B-10 31 | 15 | 2.6 | 315 | 0.15 |
| 11 | A-1 87 | EP-828 25 | 15 | 2.6 | 321 | 0.35 |
| 12 | Resin (5) for comparison | B-4 31 | 15 | 2.6 | 315 | 0.2 |

EP-828: Bisphenol A diglycidyl ether having an epoxy equivalent of 190

III. RESULTS OF PERFORMANCE TESTS

By mixing 450 parts of the compositions (aqueous dispersions each having a solids content of 20%) with 66 parts of the pigment pastes shown in Preparation Examples and 99 parts of deionized water, 20% electrodeposition baths were prepared. The compositions were electrodeposited on a lead phosphate-treated plate at a bath temperature of 28° C. and a voltage of 100 to 300 V for 3 minutes, and baked at 160° C. for 30 seconds to obtain cured coated films having a thickness of 18 to 23 microns. The results of their performances tested are shown in Table 2.

In Comparative Example 13 of Table 2, the emulsion obtained in Comparative Example 10 of Table 1 was used.

(2) Salt Resistance

A test is carried out according to JIS Z2371. When the swell of the coated film within 2.0 mm on one side of the width of the creek from the cut (linear incisure) portion of the coated film or of the portion other than the cut portion is less than 8 F (ASTM), the sample is defined as standing the test. The testing time is 1,000 and 2,000 hours.

(3) Weight Loss on Heating

The weight of the treated plate is made $W_0$. After the sample is electrodeposited on the treated plate at 30° C. for 3 minutes, the plate is dried under reduced pressure in a vacuum dryer at 80° C. for 1 hour. The weight of the dried plate is made $W_1$, and the weight after baking

TABLE 2

| Composition | | | Test results | | | | | |
|---|---|---|---|---|---|---|---|---|
|  | Pigment paste | Impact strength | Salt spray resistance | | Weight loss of heating (%) | Salt dip test at 50° C. of a film coated on an untreated plate | Condition of a coated surface | |
|  |  |  | 1000 h | 2000 h |  |  | Initial stage | After storage of a paint |
| Example |  |  |  |  |  |  |  |  |
| 9 | P-1 | acceptable | acceptable | acceptable | 4.9 | acceptable | good | good |
| 10 | P-1 | acceptable | acceptable | acceptable | 5.2 | acceptable | good | good |
| 11 | P-1 | acceptable | acceptable | acceptable | 5.0 | acceptable | good | good |
| 12 | P-1 | acceptable | acceptable | acceptable | 4.8 | acceptable | good | good |
| 13 | P-1 | acceptable | acceptable | acceptable | 4.5 | acceptable | good | good |
| 14 | P-1 | acceptable | acceptable | acceptable | 4.9 | acceptable | good | good |
| 15 | P-1 | acceptable | acceptable | acceptable | 5.6 | acceptable | good | good |
| 16 | P-1 | acceptable | acceptable | acceptable | 5.5 | acceptable | good | good |
| 17 | P-1 | acceptable | acceptable | acceptable | 4.8 | acceptable | good | good |
| 18 | P-1 | acceptable | acceptable | acceptable | 4.9 | acceptable | good | good |
| 19 | P-1 | acceptable | acceptable | acceptable | 4.9 | acceptable | good | good |
| Comparative Example |  |  |  |  |  |  |  |  |
| 10 | P-1 | unacceptable | unacceptable | unacceptable | 8.5 | unacceptable | good | good |
| 11 | P-1 | acceptable | acceptable | acceptable | 5.0 | acceptable | good | bad |
| 12 | P-1 | acceptable | acceptable | acceptable | 4.8 | unacceptable | good | good |
| 13 | P-2 | acceptable | acceptable | acceptable | 19.0 | acceptable | good | good |

Methods for testing the above performances are as follows.

(1) Impact Resistance (of the du Pont System)

The coated test plate is stored in an air-conditioned room in which the temperature is adjusted to 20°±1° C. and the humidity is adjusted to 75+2% for 24 hours. Then, on a du Pont impact tester, a cradle and an impact center of the prescribed sizes are mounted, and the sample is inserted between them with the coated surface facing upward. Next, a regular weight is caused to fall on the impact center from the prescribed height. When the coated film is free from breakage and exfoliation due to the impact, the sample is defined as standing the test.

in the dryer at 180° C. for 30 minutes is made $W_2$. The weight loss on heating W is calculated by the following equation.

$$\Delta W = \frac{W_2 - W_0}{W_1 - W_0} \times 100 \, (\%)$$

(4) Untreated Plate Salt Dip Test

A degreased untreated dull steel plate (10 cm×15 cm) was dipped in an electrodeposition bath of 10 cm. A voltage is raised from 0 V to 200 V over 10 seconds, and electrodeposition is stopped when a current of 20 coulombs passes. Backing is conducted at 160° C. for 30 minutes to obtain a cured coated film having a thickness of 18 to 22 microns.

After the coated plate is dipped in a 5% sodium chloride aqueous solution, it is left to stand at 50° C. for 20 days.

The coated film of the test plate is peeled off using a sticky tape, and a peel-off width from an edge of up to 3 mm is defined as acceptable.

(5) Paint Storage Test

After a bath paint is stirred at 30° C. for 30 days in a closed state, electrodeposition is carried out, and a cured coated film is prepared under the above conditions. The resulting cured coated film is compared with the initial coated film in a condition of a coated film.

What we claim is:

1. A resin composition for a cationically electrodepositable paint comprising
   (a) the epoxy resin derivative obtained by reacting an amine compound of the formula:

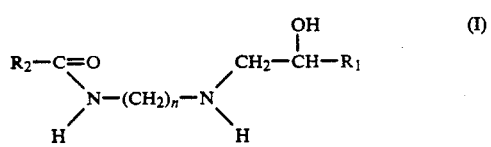

(I)

wherein n is an integer of 1 to 6; $R_1$ denotes a hydrogen atom, a methyl group or an ethyl group; and $R_2$ denotes a hydrocarbon group with 4 to 36 carbon atoms which is optionally substituted by at least one hydroxyl group and optionally contains at least one polymerizable double bond in a chain, with a first epoxy resin, and
   (b) a second epoxy resin containing, per molecule, on the average at least 2 epoxy functional groups each comprising an epoxy group directly bound to an alicyclic ring and/or bridged alicyclic ring as principal components.

2. The coating resin composition of claim 1 wherein the content of the hydroxyl groups of the amine compound is 44 to 350 calculated as a hydroxy value.

3. The coating resin composition of claim 1 wherein the content of the secondary amino groups of the amine compound is 88 to 350 calculated as an amine value.

4. The coating resin composition of claim 1 wherein the amine compound is obtained by reacting a diamine compound represented by formula

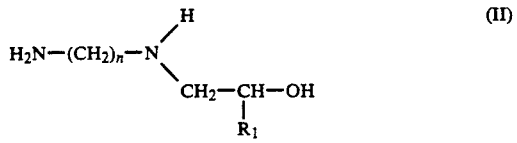

(II)

wherein $R_1$ is as defined in claim 1, with a monocarboxylic acid represented by formula $$R_2-COOH \quad \text{(III)}$$

wherein $R_2$ is as defined in claim 1.

5. The coating resin composition of claim 4 wherein the diamine compound is N-(2-hydroxyethyl)aminoethylamine.

6. The coating resin composition of claim 5 wherein the monocarboxylic acid is stearic acid, oleic acid or 12-hydroxystearic acid.

7. The coating resin composition of claim 1 wherein the epoxy resin derivative contain primary hydroxyl groups and cationic groups formed by reaction of an amine compound and epoxy groups.

8. The coating resin composition of claim 1 wherein the epoxy resin derivative is a reaction product obtained by reacting epoxy groups of said first epoxy resin formed from a polyphenol compound and epichlorohydrin with the amine compound of formula (I) either singly or in combination with a cationizing agent other than said amine compound.

9. The coating resin composition of claim 8 wherein in said first epoxy resin is a polyclycidyl ether of a polyphenyl compound having a number average molecular weight of about 800 to about 2,000 and an epoxy equivalent of 190 to 2,000.

10. The coating resin composition of claim 8 wherein said first epoxy resin is a compound represented by formula

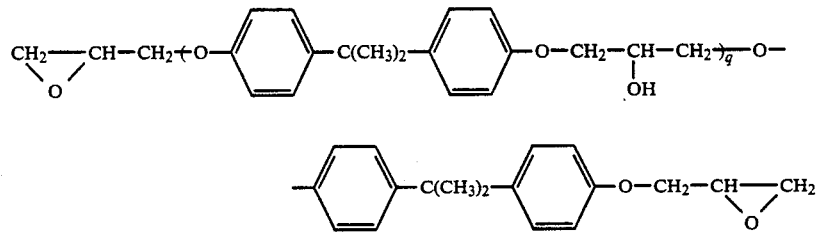

wherein q is 0 to 7.

11. The coating resin composition of claim 1 wherein the epoxy resin derivative has a hydroxyl equivalent of 20 to 5,000.

12. The coating resin composition of claim 1 wherein the epoxy resin derivative has a primary hydroxyl equivalent of 200 to 1,000.

13. The coating resin composition of claim 1 wherein the epoxy resin derivative has a cationic group-content of 3 to 200, calculated as an amine value.

14. The resin composition of claim 1 wherein said second epoxy resin (b) contains on the average at least 3 epoxy functional groups per molecule.

15. The resin composition of claim 1 wherein said second epoxy functional group of said epoxy resin (b) has a structure represented by formula (IV), (V), (VI) or (VII)

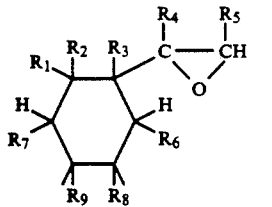

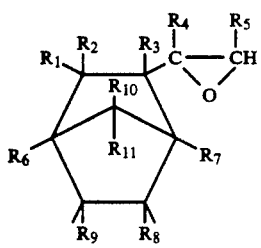

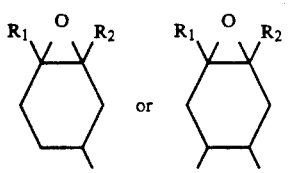

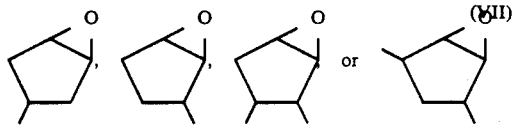

wherein $R_1$, $R_2$, $R_3$, $R_5$, $R_6$, $R_7$, $R_{10}$ and $R_{11}$ each denote H, $CH_3$ or $C_2H_5$, and $R_4$, $R_8$ and $R_9$ each denote H or $CH_3$.

16. The resin composition of claim 15 wherein said epoxy functional group is represented by formula (IV) or (V).

17. The resin composition of claim 15 wherein said epoxy functional group is represented by formula (VI) or (VII).

18. The resin composition of claim 15 wherein said second epoxy resin (b) is an epoxy resin containing at least one epoxy functional group represented by formula (IV) or (V) and at least one epoxy functional group presented by formula (VI) or (VII) in one and the same molecule or in different molecules.

19. The resin composition of claim 1 wherein said second epoxy resin (b) contains an epoxy functional group represented by formula (VIII):

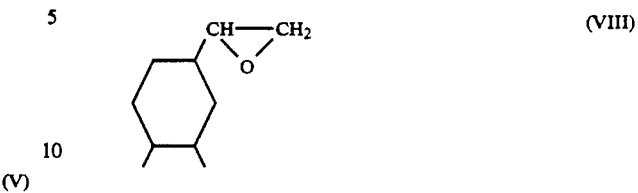

20. The resin composition of claim 1 wherein said second epoxy resin (b) has an epoxy functional group represented by formula (IX):

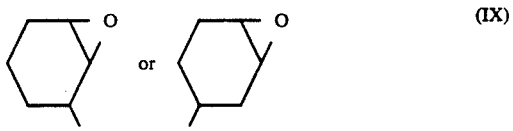

21. The resin composition of claim 1 wherein said second epoxy resin (b) has an epoxy equivalent of 100 to 2,000.

22. The resin composition of claim 21 wherein said second epoxy resin (b) has an epoxy equivalent of 150 to 500.

23. The resin composition of claim 1 wherein said second epoxy resin (b) has a number average molecular weight of 400 to 100,000.

24. The resin composition of claim 1 wherein said second epoxy resin (b) has a number average molecular weight of 700 to 50,000.

25. The resin composition of claim 1 wherein the weight ratio of the solids content of said second epoxy resin (b) to the epoxy resin derivative is 0.2 to 1.0.

26. The resin composition of claim 1 wherein at least one metallic compound selected from the group consisting of a lead compound, a zirconium compound, a cobalt compound, an aluminum compound, a manganese compound, a copper compound, a zinc compound, an iron compound, a chromium compound and a nickel compound is contained in such amount that the metal content based on the total weight of the epoxy resin derivative (A) and said second epoxy resin (b) is not more than 10% by weight.

27. A cationically electrodepositable paint containing the resin composition of claim 1.

* * * * *